(12) United States Patent
Ando et al.

(10) Patent No.: US 11,361,433 B2
(45) Date of Patent: Jun. 14, 2022

(54) IMAGE DISPLAY CONTROL SYSTEM, IMAGE DISPLAY SYSTEM, AND IMAGE ANALYSIS DEVICE FOR DYNAMIC MEDICAL IMAGING

(71) Applicant: KONICA MINOLTA, INC., Tokyo (JP)

(72) Inventors: Takanori Ando, Hachioji (JP); Kenichi Yanagisawa, Kokubunji (JP); Ichirou Hamamoto, Fuchu (JP); Naoki Hayashi, Higashimurayama (JP)

(73) Assignee: KONICA MINOLTA, INC., Tokyo (JP)

( * ) Notice: Subject to any disclaimer, the term of this patent is extended or adjusted under 35 U.S.C. 154(b) by 60 days.

(21) Appl. No.: 16/684,226

(22) Filed: Nov. 14, 2019

(65) Prior Publication Data

US 2020/0167918 A1 May 28, 2020

(30) Foreign Application Priority Data

Nov. 22, 2018 (JP) .............................. JP2018-218801

(51) Int. Cl.
*G16H 30/40* (2018.01)
*G06T 7/00* (2017.01)
*G06T 7/70* (2017.01)
*G06T 7/62* (2017.01)
(Continued)

(52) U.S. Cl.
CPC .............. *G06T 7/0012* (2013.01); *G06T 7/20* (2013.01); *G06T 7/62* (2017.01); *G06T 7/70* (2017.01); *G06T 11/206* (2013.01); *G16H 30/40* (2018.01); *G06T 2200/24* (2013.01); *G06T 2207/10124* (2013.01); *G06T 2207/20072* (2013.01); *G06T 2207/20092* (2013.01); *G06T 2207/30061* (2013.01); *G06T 2207/30101* (2013.01)

(58) Field of Classification Search
CPC .......... G06T 7/0012; G06T 7/70; G06T 7/62; G06T 11/206; G06T 7/20; G06T 2207/30061; G06T 2207/10124; G06T 2207/30101; G16H 30/40; A61B 6/465; A61B 6/464
See application file for complete search history.

(56) References Cited

U.S. PATENT DOCUMENTS

| 9,947,093 | B2 | 4/2018 | Tsunomori et al. |
| 10,242,445 | B2 | 3/2019 | Tsunomori et al. |
| 10,445,855 | B2 | 10/2019 | Harding et al. |

(Continued)

FOREIGN PATENT DOCUMENTS

| JP | 2009273671 A | 11/2009 |
| JP | 2016002251 A | 1/2016 |

(Continued)

*Primary Examiner* — Siamak Harandi
(74) *Attorney, Agent, or Firm* — Holtz, Holtz & Volek PC

(57) ABSTRACT

An image display control system includes a hardware processor that acquires data of a static image of a subject, and data of a dynamic image of the subject including a plurality of frame images, analyzes the dynamic image that is acquired, and creates analysis result data based on an analysis result, and selects, on a basis of a purpose of checking of data, at least one of the data among the data of the static image that is acquired, a part of the data of the dynamic image that is acquired, and the analysis result data that is created.

20 Claims, 16 Drawing Sheets

(51) Int. Cl.
*G06T 11/20* (2006.01)
*G06T 7/20* (2017.01)

(56) References Cited

U.S. PATENT DOCUMENTS

| | | | | |
|---|---|---|---|---|
| 2007/0166713 A1* | 7/2007 | Frieauff | ................. | G16H 40/63 |
| | | | | 435/6.13 |
| 2013/0111387 A1* | 5/2013 | Li | ......................... | G16H 30/20 |
| | | | | 715/771 |
| 2017/0032535 A1 | 2/2017 | Harding et al. | | |
| 2017/0323440 A1 | 11/2017 | Tsunomori et al. | | |
| 2018/0197289 A1 | 7/2018 | Tsunomori et al. | | |
| 2020/0104994 A1* | 4/2020 | Sharma | ................. | G06T 11/003 |

FOREIGN PATENT DOCUMENTS

| | | |
|---|---|---|
| JP | 2017510427 A | 4/2017 |
| JP | 2017200565 A | 11/2017 |

\* cited by examiner

| | | PURPOSE OF CHECKING | | | | | | |
|---|---|---|---|---|---|---|---|---|
| | | SIMPLE KINEMATIC COMPARISON | KINEMATIC COMPARISON | STRUCTURE OBSERVATION | BLOOD VESSEL OBSERVATION | SHAPING (ARM) | SHAPING (LEG) | EMERGENCY |
| EXAMINATION INFORMATION | CHEST FRONT | ○ | ○ | ○ | ○ | × | × | × |
| | CHEST SIDE | ○ | ○ | ○ | ○ | × | × | × |
| | LEG | ○ | ○ | ○ | × | × | ○ | ○ |
| | ARM | ○ | ○ | ○ | × | ○ | × | ○ |

IMAGE DISPLAY CONTROL SYSTEM, IMAGE DISPLAY SYSTEM, AND IMAGE ANALYSIS DEVICE FOR DYNAMIC MEDICAL IMAGING

BACKGROUND

Technological Field

The present invention relates to an image display control system, an image display system, and an image analysis device.

Description of the Related Art

Moving image radiographing (also referred to as continuous radiographing) is used as one radiographing method for radiographs.

In moving image radiographing, a plurality of frame images are repeatedly created at a predetermined cycle (such as 15 times per second). Observation of motion of a radiographing target part (such as a lung field) is enabled by reproduction on a display device of a dynamic image that is obtained by the moving image radiographing (i.e. sequential display of the plurality of frame images).

In recent years, visibility of a radiographing target part is increased, or motion of a radiographing target part is followed in detail, for example, by subjecting image data of a dynamic image to various image analyses as described in JP-A-2017-510427, JP 2016-002251 A, JP 2009-273671 A, and JP 2017-200565 A.

Generally, a doctor sees a large number of examined persons a day, and a consultation time per person tends to be limited in many cases.

A dynamic image includes a large number of frame images, and also, a plurality of types of image analyses are sometimes performed on one dynamic image, as described above. Accordingly, at the time of consultation using a dynamic image, a doctor has to perform various operations of selecting an analysis result that he/she wants to check, looking for a frame image that he/she wants to check from the dynamic image, and reproducing a dynamic image and measuring a time taken by predetermined motion, for example, and there is a problem that consultation takes time.

SUMMARY

An object of the present invention has been achieved in view of the problem described above, and is to reduce a time of consultation performed using a dynamic image than conventionally required.

To achieve at least one of the abovementioned objects, according to a first aspect of the present invention, an image display control system reflecting one aspect of the present invention comprises a hardware processor that:

acquires data of a static image of a subject, and data of a dynamic image of the subject including a plurality of frame images, analyzes the dynamic image that is acquired, and creates analysis result data based on an analysis result, and selects, on a basis of a purpose of checking of data, at least one piece of data among the data of the static image that is acquired, a part of the data of the dynamic image that is acquired, and the analysis result data that is created.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiment of the present invention will be described with reference to the drawings. However, the scope of the invention is not limited to the disclosed embodiments.

Image Display System

Figure 1:
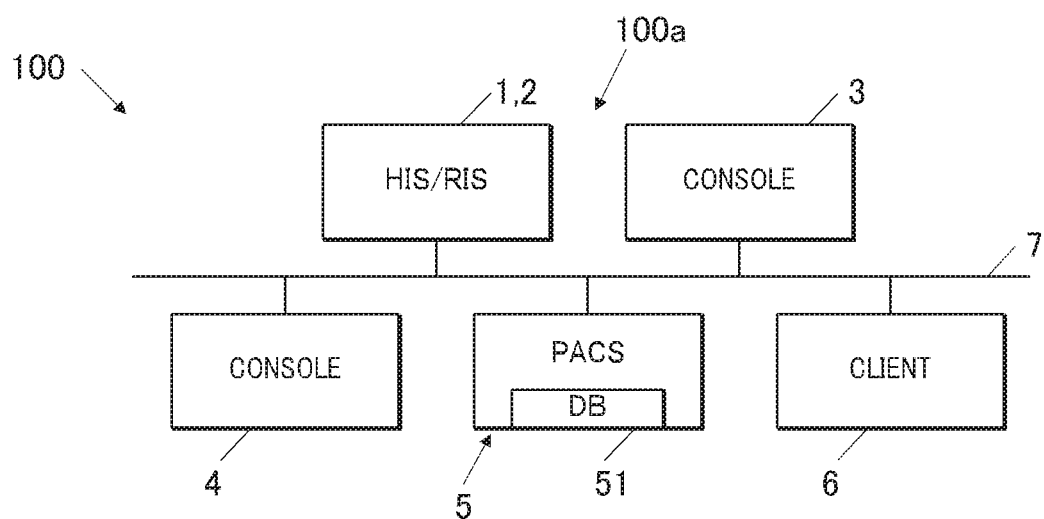
FIG. 1 is a block diagram showing an image display system according to an embodiment of the present invention.

First, a schematic configuration of an image display system according to a present embodiment be described. FIG. 1 is a block diagram showing an image display system 100.

As shown in FIG. 1, the image display system 100 of the present embodiment includes a hospital information system (hereinafter "HIS 1"), a radiology information system (hereinafter "RIS 2"), a console 3, an image analysis device 4, a picture archiving and communication system (hereinafter "PACS 5"), and a client 6.

These are capable of communicating with one another over a communication network 7.

Furthermore, in the present embodiment, the HIS 1, the RIS 2, the console 3, the image analysis device 4, and the PACS 5 form an image display control system 100a.

Furthermore, the image display system 100 is connected to a modality, not shown, over the communication network 7.

The modality may be any modality as long as it is capable of creating a dynamic image including a plurality of frame images, and a panel-shaped radiographic imaging apparatus or the like may be used, for example.

Additionally, instead of being directly connected to the communication network 7, the modality may be connected through another device (such as the console 3, the image analysis device 4, the PACS 5, or the like).

Furthermore, transfer of images from the modality to the image display system 100 may be performed using a storage medium or a cable, instead of through the communication network.

The HIS 1 and the RIS 2 store examination information.

In the present embodiment, the "examination information" refers to the type of radiographing (the type of modality used, upright position/recumbent position, etc.), a radiographing target part, the name of a clinical department requesting for examination, age of an examined person, sex of the examined person, the name of an operator, and the like.

Additionally, a description is given here of a case where all the above items are included in the examination information, but it is sufficient if the examination information includes at least one of the items.

Moreover, in response to a request from another device or the like (such as the console 3, the image analysis device 4, the PACS 5, or the client 6), the HIS 1 and the RIS 2 transmit the examination information according to the request to the other device or the like.

The console 3 according to the present embodiment is configured by a PC or a dedicated device.

Furthermore, the console 3 is capable of setting various radiographing conditions (such as a tube voltage, a tube current, a radiation time (mAs value), a frame rate, and the like) in the modality or the like, on the basis of the examination information acquired from another device or the like (such as the HIS 1 or the RIS 2) or an operation by an operator.

The image analysis device 4 is configured by a PC or a dedicated device.

Furthermore, the image analysis device 4 is capable of analyzing a static image or a dynamic image acquired from the modality, and of creating analysis result data based on an analysis result.

Details of the image analysis device 4 and the analysis result data will be given later.

The PACS 5 according to the present embodiment is configured by a PC or a dedicated device.

Furthermore, the PACS 5 includes a database 51, and is capable of storing the static image or the dynamic image acquired from the modality, the analysis result data created by the image analysis device 4, and the like in the database 51.

Details of the analysis result data will be given later.

Moreover, in response to a request from another device or the like (such as the console 3, the image analysis device 4, or the client 6), the PACS 5 transmits an image or data according to the request, among various images and various types of data stored in the database 51, to the other device or the like.

Additionally, the database 51 may be provided as a device separate from the PACS 5.

The client 6 according to the present embodiment is a tablet terminal or the like, and may be carried by an operator.

Details of the client 6 will also be given later.

Image Analysis Device

Figure 2:
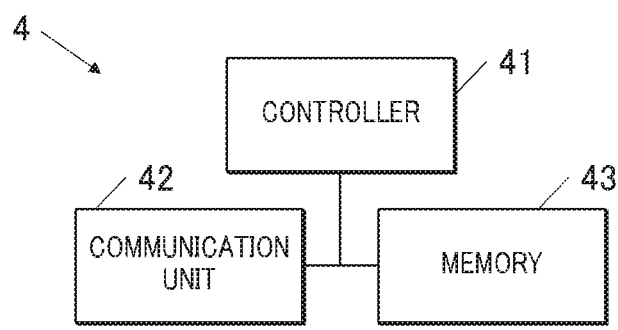
FIG. 2 is a block diagram showing an example of an image analysis device provided in the image display system in FIG. 1.

Next, a specific configuration of the image analysis device 4 provided in the image display system 100 described above will be described. FIG. 2 is a block diagram showing the image analysis device 4.

As shown in FIG. 2, the image analysis device 4 according to the present embodiment includes a controller 41, a communication unit 42, and a memory 43.

The controller 41 is configured by a central processing unit (CPU), a random access memory (RAM), and the like. The CPU of the controller 41 controls operation of each unit of the image analysis device 4 in a centralized manner by reading out, and developing in the RAM, various programs stored in the memory 43, and by performing various processes according to the developed programs.

The communication unit 42 is configured by a wireless module or the like, and is capable of exchanging various signals and various types of data with other devices 1 to 3, 5, and 6 that are connected over the communication network 7 (a local area network (LAN), a wide area network (WAN), the Internet, or the like).

The memory 43 is configured by a non-volatile semiconductor memory, a hard disk, or the like, and stores various programs to be executed by the controller 41, parameters necessary to execute the programs, and the like.

Furthermore, the memory 43 stores various purposes of checking.

The "purpose of checking" is a purpose of an examining person (doctor) for viewing a dynamic image or the like, and the purposes in the present embodiment are simple kinematic comparison, kinematic comparison, structure observation, blood vessel observation, follow-up observation, shaping, and emergency.

Additionally, a description is given here of a case where all the above items are included in the purpose of checking, but it is sufficient if the purpose of checking includes at least one of the items.

Of the above, "simple kinematic comparison" is comparison between a still subject and a moving subject.

Furthermore, "kinematic comparison" is comparison between a subject in a certain state and the subject in another state.

Still further, "structure observation" is observation of motion of a specific structure (such as a lung) in a subject.

Still further, "blood vessel observation" is observation of a state of a blood vessel in a subject.

Still further, "follow-up observation" is observation of a change in state of a subject from a past state.

Still further, "shaping" is comparison between different states of bones in a subject (such as a state in which a joint is bent and a state in which the joint is extended, a load state in an upright position and the load state in a recumbent position, etc.).

Still further, "emergency" is observation of a subject over a wide range for specification of an abnormal part of an emergency patient.

Moreover, the memory 43 stores at least one type of analysis result data in association with the purpose of checking.

Details of the analysis result data will be given later.

Furthermore, in the present embodiment, in addition to the analysis result data, the static image and the dynamic image are also associated with the purpose of checking.

Furthermore, in addition to a type of the analysis result data, the memory 43 stores, in association with the purpose of checking, at least one of the number of displays used to display a check screen S described later, types of buttons to be displayed on the check screen S, a layout of the check screen S, a display timing of data, a display order of data, a display time of data, a display size of data, a color scheme at the time of display, assignment of a function to an operation unit 65 or the like of the client 6 described later, or a radiographing period of a static image or a dynamic image.

Figures 3, 4:
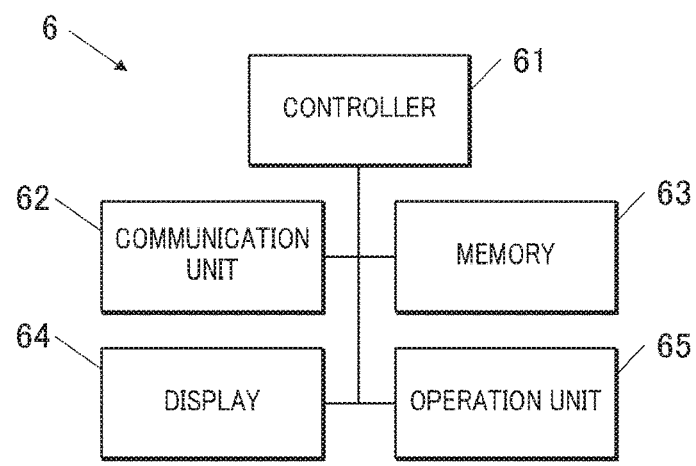
FIG. 3 is a table showing an example of correspondence relationship between examination information and a purpose of checking that can be selected, stored in a memory provided in the image display system in FIG. 1.
FIG. 4 is a block diagram showing an example of a display device provided in the image display system in FIG. 1.

Furthermore, the memory 43 stores a correspondence relationship between the examination information and a purpose of checking that can be selected, in the form of a table as shown in FIG. 3, for example.

Additionally, instead of being stored in the memory 43, the correspondence relationship table may be stored in another device or the like (such as the client 6 described later) used to select a purpose of checking.

The controller 41 of the image analysis device 4 configured in the above manner includes functions as described below.

For example, the controller 41 includes a function of acquiring data of a static image of a subject and data of a dynamic image of the subject from other devices and the like (such as the modality, the console 3, the image analysis device 4, and the like) through the communication unit 42.

Furthermore, the controller 41 includes a function of analyzing an acquired dynamic image, and of creating analysis result data based on an analysis result.

In the present embodiment, a plurality of pieces of analysis result data of different types may be created.

In the present embodiment, the "analysis result data" is an analyzed dynamic image that is created by applying an analysis result, as an image processing parameter, to a dynamic image, a specific frame image that is specified on the basis of the analysis result from a plurality of frame images forming a dynamic image or the analyzed dynamic image, an analysis measurement value that is obtained on the basis of the analysis result, and an analysis graph that is obtained on the basis of the analysis result.

Additionally, a description is given here of a case where all the above items are included in the analysis result data, but it is sufficient if the analysis result data includes at least one of the items.

Furthermore, in the present embodiment, the "analysis measurement value" indicates a position of a specific point of a specific structure in a subject, a distance between the specific point and another point, an area of the specific structure, a volume of the specific structure, a signal value of a predetermined pixel of the subject, a maximum signal value in a predetermined range in a frame image, a minimum signal value in the predetermined range, an average value of all the signal values in the predetermined range, a cardiothoracic ratio, and an arrangement angle of the specific structure in a frame image (such as a bending angle of a joint, or a rotation angle (tilt relative to a reference) of a bone or an organ).

Additionally, a description is given here of a case where all the above items are included in the analysis measurement value, but it is sufficient if the analysis measurement value includes at least one of the items.

Furthermore, in the present embodiment, the "specific frame image" is a frame image, among a plurality of frame images, that is a frame image with a greatest analysis measurement value, a frame image with a smallest analysis measurement value, a frame image, the analysis measurement value of which coincides with an average value, a frame image, the analysis measurement value of which is within a predetermined range, a frame image, the analysis measurement value of which coincides with a predetermined value, or a frame image selected by an operator.

Additionally, in the case where a static image is included for the same examination, the "specific frame image" may be a frame image, the analysis measurement value of which is closest to the analysis measurement value of the static image, or a frame image, the analysis measurement value of which is farthest from the analysis measurement value of the static image, among the plurality of frame images.

Moreover, in the case where an analysis target dynamic image is obtained by radiographing a structure that periodically repeats a predetermined motion (such as a lung that repeats expansion/contraction), the "specific frame image" may be a frame image, in each cycle, that is a frame image with a greatest analysis measurement value, a frame image with a smallest analysis measurement value, a frame image, the analysis measurement value of which coincides with an average value, a frame image, the analysis measurement value of which is within a predetermined range, a frame image, the analysis measurement value of which coincides with a predetermined value, or a frame image selected by an operator. In this case, a plurality of specific frame images are obtained from one dynamic image.

Moreover, the "analysis graph" is a graph that is created on the basis of the analysis measurement value.

Specifically, the analysis graph is a graph with the number of frames on a horizontal axis, and the analysis measurement value on a vertical axis.

Moreover, the controller 41 according to the present embodiment is capable of subjecting the dynamic image to a plurality of types of analyses.

Specifically, at least one of specific component difference processing, frequency enhancement processing, specific component tracking processing, specific signal change amount extraction processing, specific similar waveform pattern extraction processing, or integrated image difference processing is performed.

Of these, the "specific component difference processing" is a process of increasing visibility of a region other than a specific region (such as a rib bone or a collarbone in a lung field) of a radiographing target part by reducing a signal value of the specific region.

Furthermore, the "frequency enhancement processing" is a process of making a specific region of a radiographing target part clear by enhancing a frequency at an edge of the specific region.

Furthermore, the "specific component tracking processing" is a process of calculating an amount of movement or a speed of a specific region (such as a diaphragm) of a radiographing target part, or of calculating a distance between two different specific regions (such as between an apex of a lung and a diaphragm), for example.

Furthermore, the "specific signal change amount extraction processing" is a process of visualizing an amount of change in a signal value using colors.

Furthermore, the "specific similar waveform pattern extraction processing" is a process of visualizing a degree of similarity to a specific signal change using colors.

Furthermore, the "integrated image difference processing" is a processing of visualizing a total amount of signal change in radiographing, by displaying a difference between an integrated image of a maximum signal value and an integrated image of a minimum signal value.

Additionally, a plurality of such analyses may be performed in combination.

Furthermore, the analyzed dynamic image, the specific frame image, the analysis measurement value, and the analysis graph may be created for each analysis.

Furthermore, the controller 41 includes a function of specifying one of a plurality of purposes of checking stored in the memory 43.

Specification of a purpose of checking may be automatically performed by the controller 41 itself, or may be manually performed by an operator.

In the case of being automatically performed, specification is performed on the basis of the analysis result data created by the controller 41, the examination information received from the HIS 1 or the RIS 2, or the like.

Moreover, in the case of being manually performed, specification is performed on the basis of an operation performed on the operation unit 65 of the client 6 described later (such as a touch or a click on a purpose-of-checking switching section Sg) or the like.

Furthermore, in the case of manual performance, a timing of selection may be before or after acquisition of the dynamic image.

Moreover, the controller 41 includes a function of changing a specified purpose of checking on the basis of an operation performed by an operator.

Specifically, the purpose of checking is changed to that according to a purpose change signal transmitted from the client 6 in response to an operator operating the operation unit 65 of the client 6 described later (by touching or clicking on the purpose-of-checking switching section Sg described later, for example).

Additionally, in the case where an operation unit is provided in the console 3, the image analysis device 4, or the PACS 5, manual selection or change of the purpose of checking may be performed using such an operation unit.

Moreover, the controller 41 includes a function of selecting, on the basis of a specified purpose of checking, at least one piece of data among data of an acquired static image, data of an acquired dynamic image, and the created analysis result data.

Specifically, data that is associated with the specified purpose of checking, among the stats; dynamic image, and a plurality of pieces of analysis result data, is selected.

For example, in the case where the selected purpose of checking is "simple kinematic comparison", data of a static image, data of a dynamic image or an analyzed dynamic image, and data of analysis measurement values are selected.

Furthermore, in the case where the selected purpose of checking is "kinematic comparison", data of one specific frame image in a dynamic image or an analyzed dynamic image, data of another specific frame image, data of an analysis graph, and data of analysis measurement values are selected.

Still further, in the case where the selected purpose of checking is "structure observation", data of a dynamic image or an analyzed dynamic image, data of an analysis graph, and data of analysis measurement values are selected.

Still further, in the case where the selected purpose of checking is "blood vessel observation", data of an analyzed dynamic image obtained by performing the specific component difference processing, data of an analysis graph, and data of analysis measurement values are selected.

Still further, in the case where the selected purpose of checking is "follow-up observation", data of a plurality of dynamic images or analyzed dynamic images obtained by performing radiographing during several examinations, data of an analysis graph, and data of analysis measurement values are selected.

Still further, in the case where the selected purpose of checking is "shaping", at least one piece of data among data of a static image obtained by radiographing each of different states of a same part of an examined person, data of a dynamic image, data of a long static image obtained by synthesizing a plurality of static images, and data of a long dynamic image obtained by synthesizing a plurality of dynamic images is selected.

Still further, in the case where the selected purpose of checking is "emergency", at least one piece of data among data of a static image obtained by radiographing each of different parts of an examined person, data of a dynamic image, data of a long static image obtained by synthesizing a plurality of static images, and data of a long dynamic image obtained by synthesizing a plurality of dynamic images is selected.

Additionally, in the present embodiment, a piece of data may be selected on the basis of the purpose of checking and the examination information, instead of only on the purpose of checking.

For example, in the case where the selected purpose of checking is "simple kinematic comparison", and the examination information is "chest/front (radiographing target part)", a process of selecting static image data, data of a dynamic image or an analyzed dynamic image, and data of analysis measurement values for "chest" is performed.

This allows further dividing of selection patterns of various pieces of data, and narrowing down of various pieces of data associated with a combination of the purpose of checking and the examination information, and an examining person may more accurately select information he/she desires to check.

Moreover, the controller 41 includes a function of transmitting selected data to the client 6 through the communication unit 42.

Moreover, the controller 41 includes a function of transmitting data of a specific frame image according to a frame request signal transmitted from the client 6, to the client 6 through the communication unit 42, in response to an operator operating the operation unit 65 of the client 6 described, later (by touching or clicking on a point on a line in an analysis graph G described later).

Heretofore, a specific configuration of the image analysis device 4 according to the present embodiment has been described, but at least a part of various functions of the image analysis device 4 may be implemented by the console 3 or the PACS 5.

Furthermore, the image display control system 100a does not have to be configured by all of the devices 1 to 5 described above, and may alternatively be configured by only a device including the function of acquiring data of a static image of a subject and data of a dynamic image of the subject, the function of analyzing the acquired data of the dynamic image and creating the analysis result data based on the analysis result, and the function of selecting, on the basis of the purpose of checking data, at least one of the data among the acquired data of the static image, at least a part of the acquired data of the dynamic image, and the created analysis result data.

Client

Next, a specific configuration of the client 6 provided in the image display control system 100*a* described above will be described. FIG. 4 is a block diagram showing a configuration of the client 6.

As shown in FIG. 4, the client 6 according to the present embodiment includes a controller 61, a communication unit 62, a memory 63, a display 64, and the operation unit 65.

The controller 61 and the communication unit 62 are configured in a similar manner as the controller 41 and the communication unit 42 of the image analysis device 4.

The memory 63 is configured by a non-volatile semiconductor memory, a hard disk, or the like, and stores various programs to be executed by the controller 61, parameters necessary to execute the programs, and the like.

The display 64 is configured by a monitor such as a liquid crystal display (LCD), a cathode ray tube (CRT), or the like, and displays various images, various pieces of information, and the like as instructed by a display signal input from the controller 61.

An operator may operate the operation unit 65 through a keyboard including cursor movement keys, numeric keys, various function keys, and the like, a pointing device such as a mouse, a touch panel stacked on a surface of the display 64, and the like.

Furthermore, the operation unit 65 outputs, to the controller 61, various signals (a purpose change signal and a frame request signal described later) based on operations performed by the operator.

Additionally, an operation unit may be provided in the console 3, the image analysis device 4, the PACS 5, or the like, instead of providing the operation unit 65 in the client 6.

The controller 61 of the client 6 configured in the above manner includes functions as described below.

For example, the controller 61 includes a function of receiving the data selected by the image analysis device 4, through the communication unit 62.

Furthermore, the controller 61 includes a function of causing the display 64 to display a check screen S.

Figure 5:
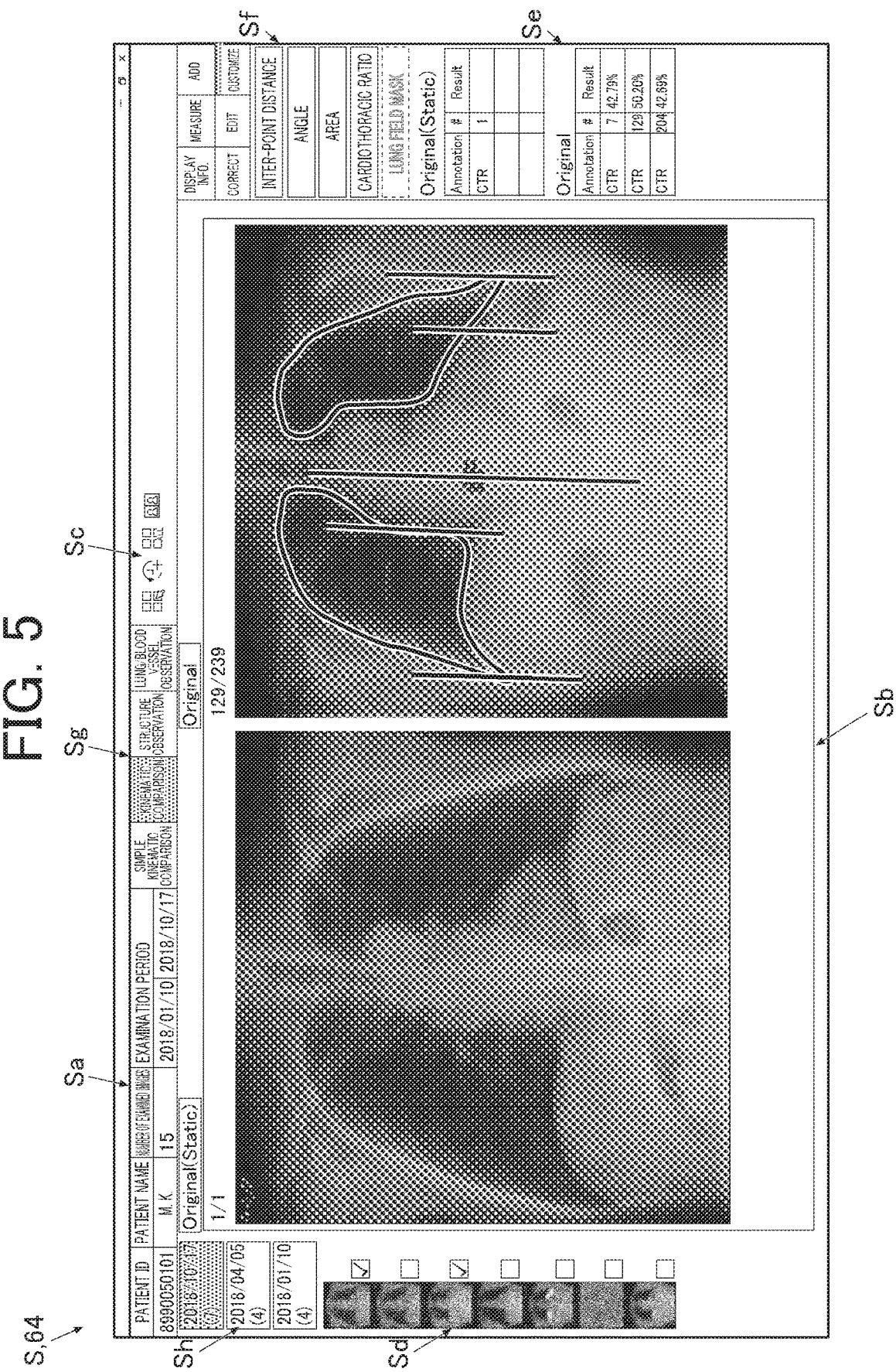
FIG. 5 is an example of a screen displayed on the display device in FIG. 4.

For example, as shown in FIG. 5, the check screen S in the present embodiment includes an examination information display section Sa, an image display section Sb, an image display switching section Sc, a thumbnail display section Sd, a numerical value display section Se, a numerical value display switching section Sf, a purpose-of-checking switching section Sg, and an examination switching section Sh.

Of these, the examination information display section Sa is a region for displaying the examination information regarding an examined person.

Furthermore, the image display section Sb is a region for displaying a dynamic image or an analyzed dynamic image of the examined person, or an analysis graph G that is one piece of analysis result data.

Furthermore, the image display switching section Sc is a region where various buttons for switching between display modes of the image display section Sb are provided.

Furthermore, the thumbnail display section Sd is a region for displaying a list of thumbnails of dynamic images and various analyzed dynamic images from a same examination.

Still further, the numerical value display section Se is a region for displaying an analysis measurement value that is one piece of analysis result data.

Still further, the numerical value display switching section Sf is a region where buttons for selecting analysis measurement values to be displayed from a plurality of types of analysis measurement values are provided.

Still further, the purpose-of-checking switching section Sg is a region where various buttons used for switching between the purposes of checking are provided.

Still further, the examination switching section Sh is a region where various buttons used for switching between examinations to be checked are provided.

Additionally, the purpose-of-checking switching section Sg according to the present embodiment is in accordance with the table described above showing a correspondence relationship between the examination information and the purpose of checking that can be selected (see FIG. 3), and disables operation of a button for a purpose of checking that cannot be operated, or hides or grays out such a button.

Furthermore, the controller 61 includes a function of displaying the check screen S based on received data, in a layout according to the purpose of checking.

In the present embodiment, display is performed on the display 64, as shown in FIGS. 6 to 11, for example.

Figure 6:
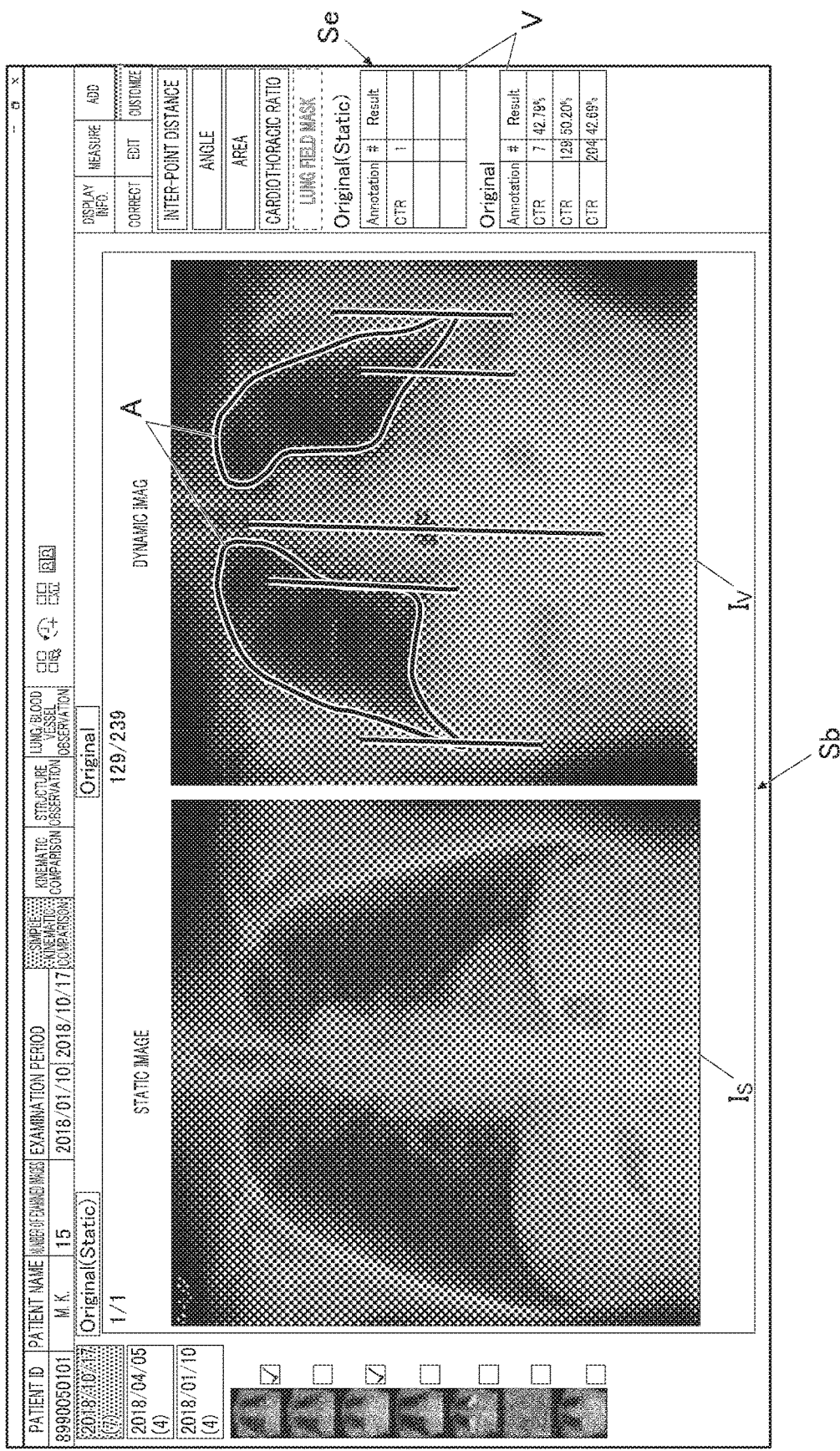
FIG. 6 is an example of a screen displayed on the display device in FIG. 4.
Figure 7:
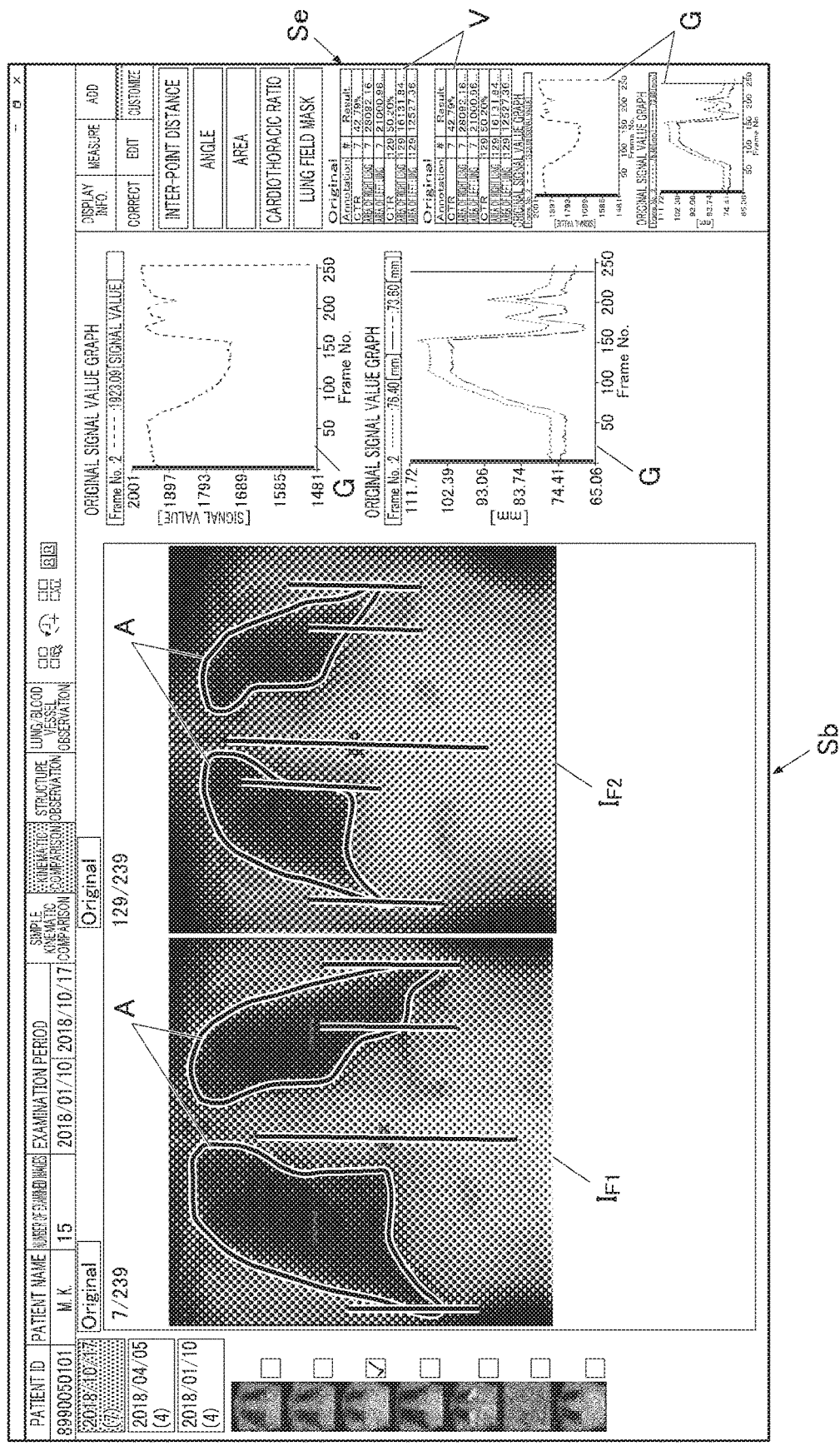
FIG. 7 is an example of a screen displayed on the display device in FIG. 4.
Figure 8:
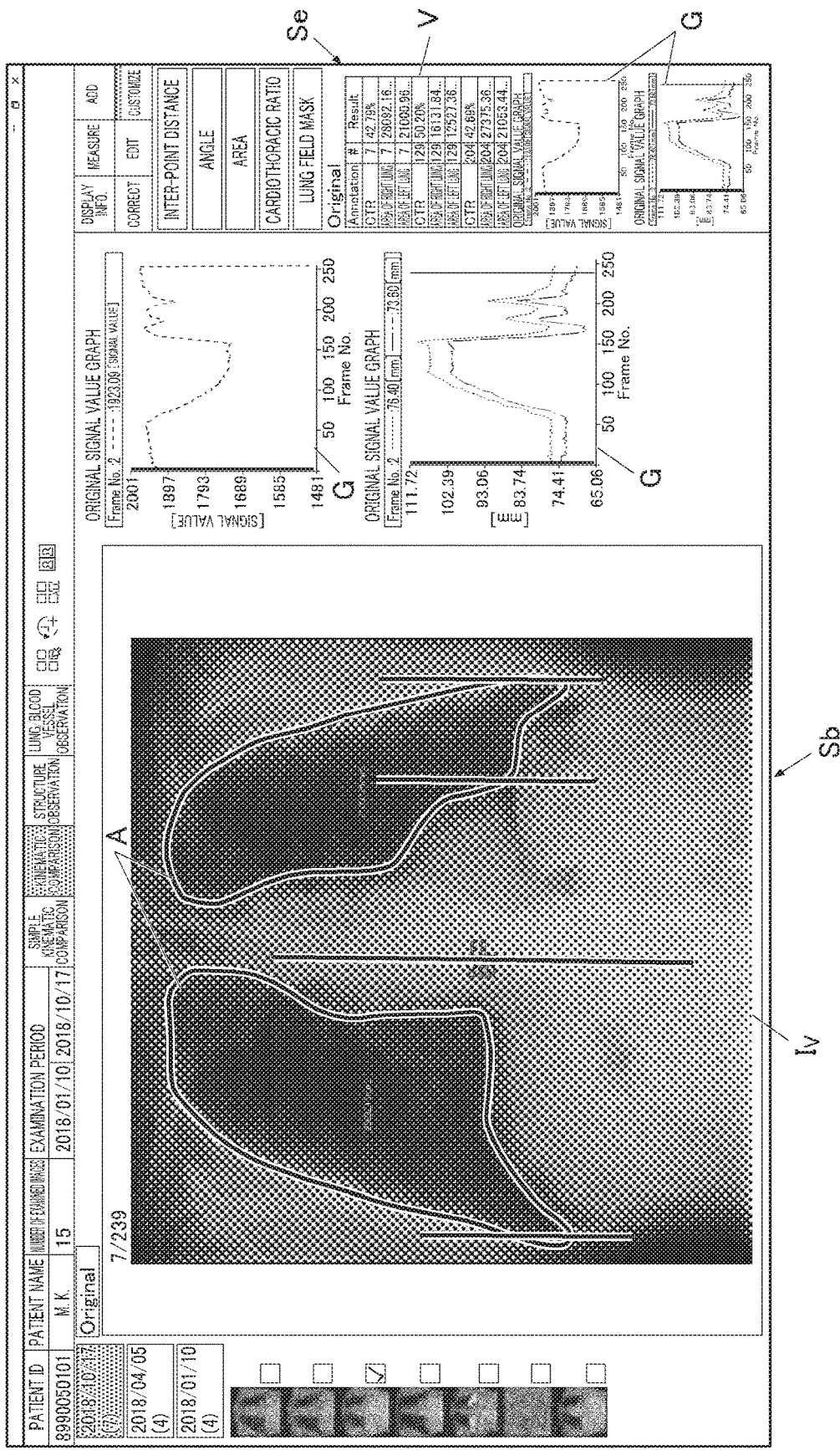
FIG. 8 is an example of a screen displayed on the display device in FIG. 4.

For example, as shown in FIG. 6, in the case where the selected purpose of checking is "simple kinematic comparison", a static image IS, a dynamic image IV or an analyzed dynamic image IA (FIGS. 6 to 8 show a case where annotations A based on analysis measurement values V are displayed superimposed on the dynamic image IV) are displayed in the image display section Sb, and the analysis measurement values V are displayed in the numerical value display section Se.

Furthermore, as shown in FIG. 7, in the case where the selected purpose of checking is "kinematic comparison", one specific frame image IF1 in a dynamic image IV or an analyzed dynamic image IA, another specific frame image IF2, and analysis graphs G are displayed in the image display section Sb, and analysis measurement values V are displayed in the numerical value display section Se.

Additionally, in "kinematic comparison", a specific frame image IF2 showing a state that is most different from that of the one specific frame image IF1 is desirably displayed. For example, in the case where the dynamic image is capturing a chest, if a state where the lungs are most expanded is displayed as the one specific frame image IF1, a state where the lungs are most contracted is displayed as the other specific frame image IF2.

Furthermore, as shown in FIG. 8, in the case where the selected purpose of checking is "structure observation", a dynamic image IV or an analyzed dynamic image IA and analysis graphs G are displayed in the image display section Sb, and analysis measurement values V are displayed in the numerical value display section Se.

Figure 9:
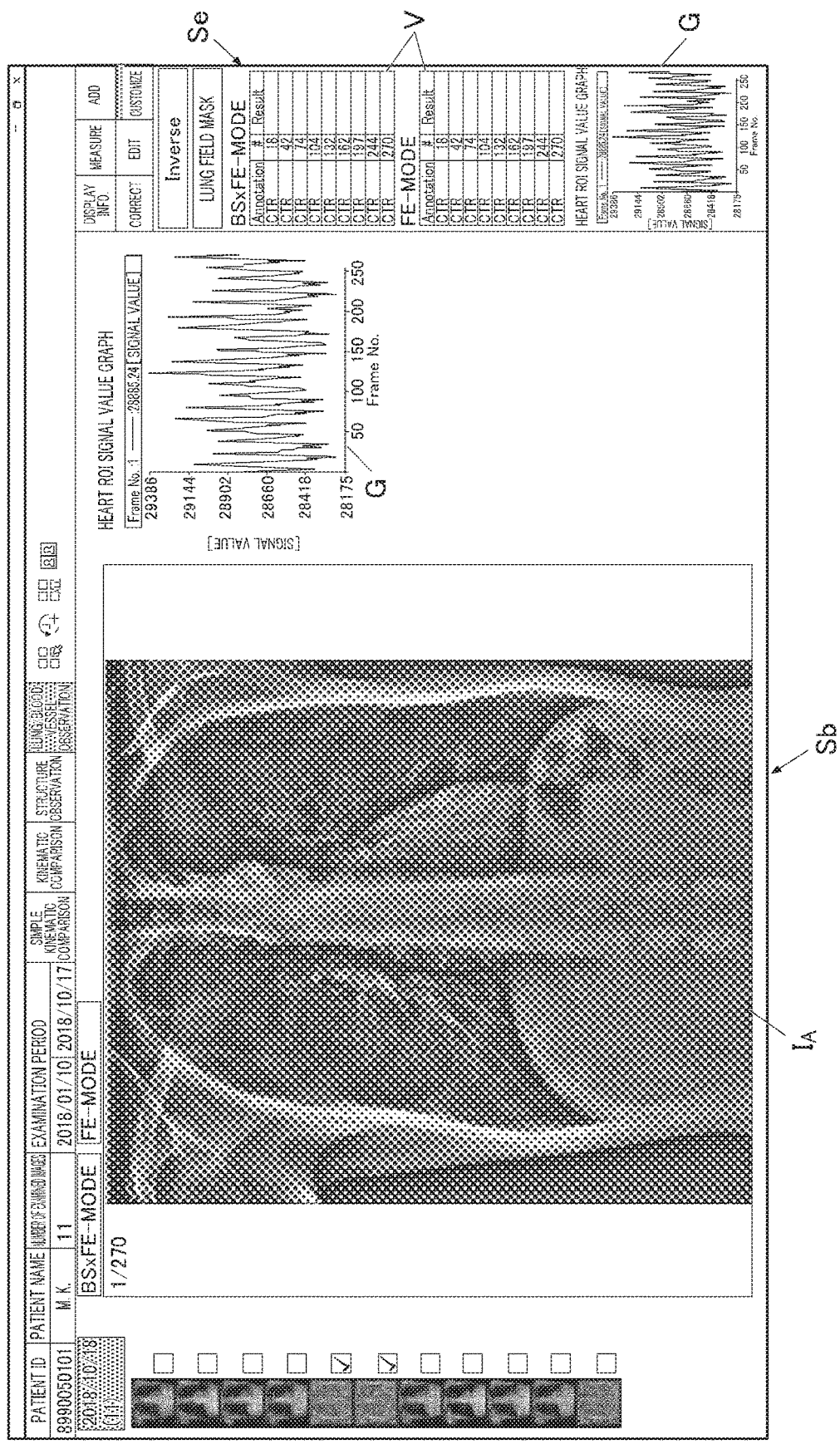
FIG. 9 is an example of a screen displayed on the display device in FIG. 4.

Furthermore, as shown in FIG. 9, in the case where the selected purpose of checking is "blood vessel observation", an analyzed dynamic image IA obtained by applying the specific component difference processing a dynamic image IV and an analysis graph G are displayed in the image display section Sb, and analysis measurement values V are displayed in the numerical value display section Se.

Figure 10:
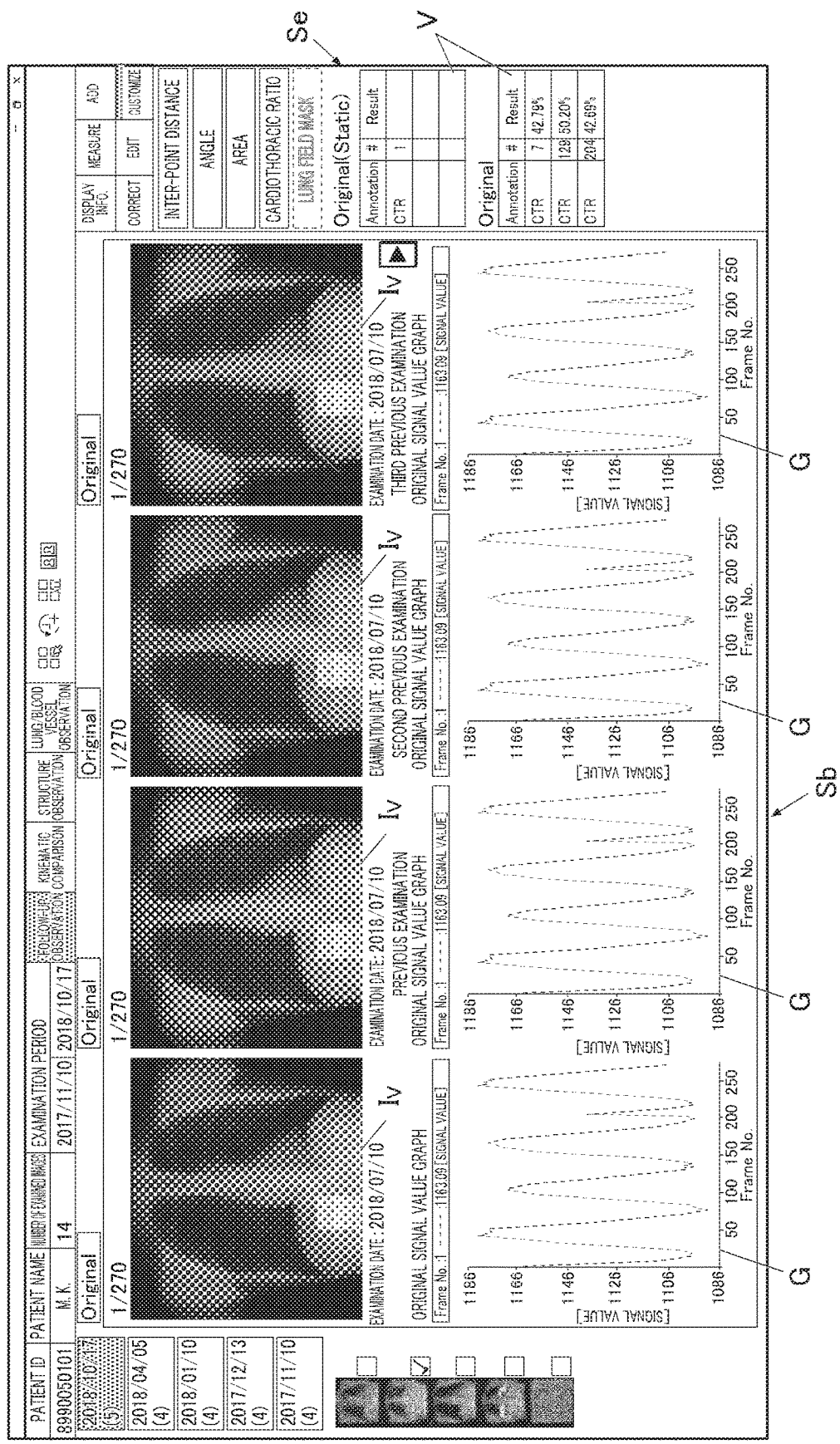
FIG. 10 is an example of a screen displayed on the display device in FIG. 4.

Furthermore, as shown in FIG. 10, in the case where the selected purpose of checking is "follow-up observation", a plurality of dynamic images IV obtained by performing radiographing during several examinations or a plurality of analyzed dynamic images IA of a same type and an analysis graph corresponding to each dynamic image IV, IA are displayed in the image display section Sb, and analysis measurement values V are displayed in the numerical value display section Se.

Furthermore, in the case where the selected purpose of checking is "shaping", at least one of a static image IS obtained by radiographing each of different states of a same part of an examined person, a dynamic image IV, a long static image ILS, or a long dynamic image ILV is displayed in the image display section Sb.

Figure 11:
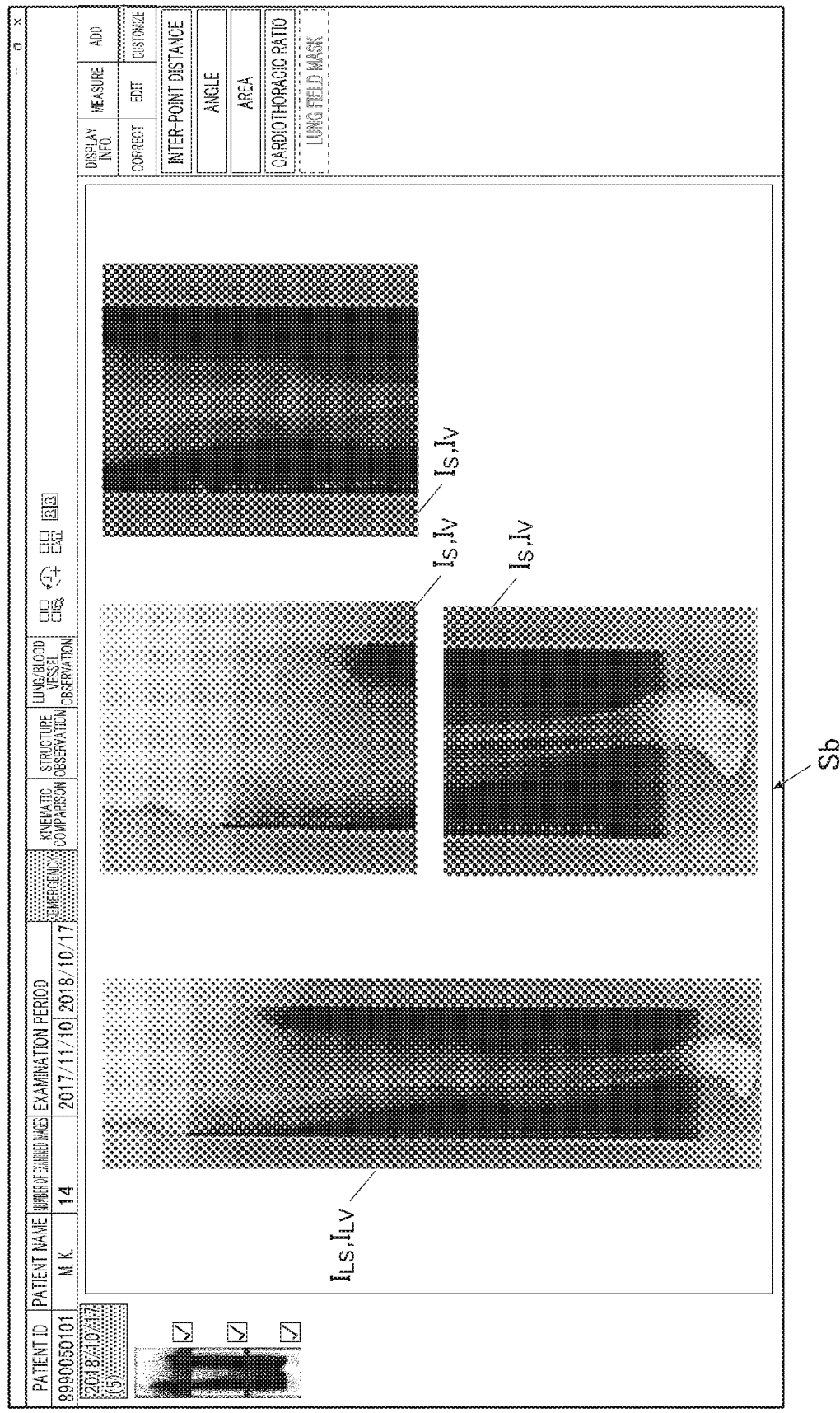
FIG. 11 is an example of a screen displayed on the display device in FIG. 4.

Furthermore, as shown in FIG. 11, in the case where the selected purpose of checking is "emergency", at least a plurality of static images IS obtained by radiographing different parts of a subject, a dynamic image IV, a long static image ILS, or a long dynamic image ILV is displayed in the image display section Sb.

Additionally, as in the present embodiment, by including "layout of the check screen S" and "display size of data" as targets to be associated with the purpose of checking, a check target which is to be checked first (or importance of which is the highest) may be displayed with a relatively large size, and a check target which is to be checked next (or importance of which is relatively low) may be displayed with a relatively small size, below or beside the check target that is displayed with a large size, with respect to a combination of at least two check targets among the images IS, IV, IA and the graph G, for example.

Furthermore, as in the present embodiment, by including "color scheme at the time of display" as a target to be associated with the purpose of checking, a check target which is to be checked first (or importance of which is the highest) may be displayed with a more striking hue compared to other check targets.

Furthermore, as in the present embodiment, by including "types of buttons to be displayed on the check screen S" and "assignment of a function to an operation unit" as targets to be associated with the purpose of checking, for example, in the case where a purpose of checking for which a static image IS or a graph G is mainly displayed is selected, operation of the operation unit 65 or the like (enlargement/reduction of an image or a graph, or parallel movement of an image or a graph (pan function) based on such operation) may be performed, or in the case where a purpose of checking for which a dynamic image IV is mainly displayed is selected, reproduction/stop may be performed on the basis of operation of the operation unit 65 or the like, or short-cut buttons for such operations may be displayed on the check screen S.

Furthermore, as in the present embodiment, by including "age of an examined person" and "sex of an examined person" in the examination information, the check screen S may be displayed taking into account a difference in analysis method according to a physical difference between a baby and an adult or a difference in the type of radiographing according to pregnancy/non-pregnancy, for example.

Furthermore, by including "operator" in the examination information, taste of each operator may be reflected in the layout of the check screen S.

Furthermore, as in the present embodiment, by including a radiographing period as a target to be associated with the purpose of checking, a dynamic image obtained in the past by examining a same examined person (such as "dynamic image of previous radiographing", "dynamic image radiographed a year before" or "another dynamic image obtained by performing radiographing on a same day") may be included as a comparison target.

Additionally, display contents for each purpose of checking described above are only exemplary, and it is also possible to display only the static image IS, only a part of the dynamic image (including the specific frame image IF), only the analyzed dynamic image IA, only the analysis measurement value V, or only the analysis graph G. or a combination that includes at least two of the above and that is not described above.

Moreover, the controller 61 includes a function of receiving change of the purpose of checking, through the operation unit 65.

If change of the purpose of checking is received, the controller 61 transmits a purpose change signal indicating the purpose of checking after change, to the image analysis device 4 through the communication unit 62.

When the purpose change signal is transmitted, various pieces of data according to the purpose of checking after change are transmitted from the image analysis device 4, and thus, the controller 61 displays, on the display 64, at least one of the static image IS, the dynamic image IV, the analyzed dynamic image IA, the analysis graph G, or the analysis measurement value V, according to the request.

Moreover, the controller 61 includes a function of switching, in accordance with change of the purpose of checking, the layout of the check screen S to that according to the purpose of checking after change.

Additionally, the function of determining/changing the layout of the check screen S may be provided in the image analysis device 4 or the like, instead of the controller 61.

Moreover, the controller 61 includes a function of receiving, through the operation unit 65, a request regarding a specific frame image IF that is desired to be displayed in a dynamic image.

Figure 12:
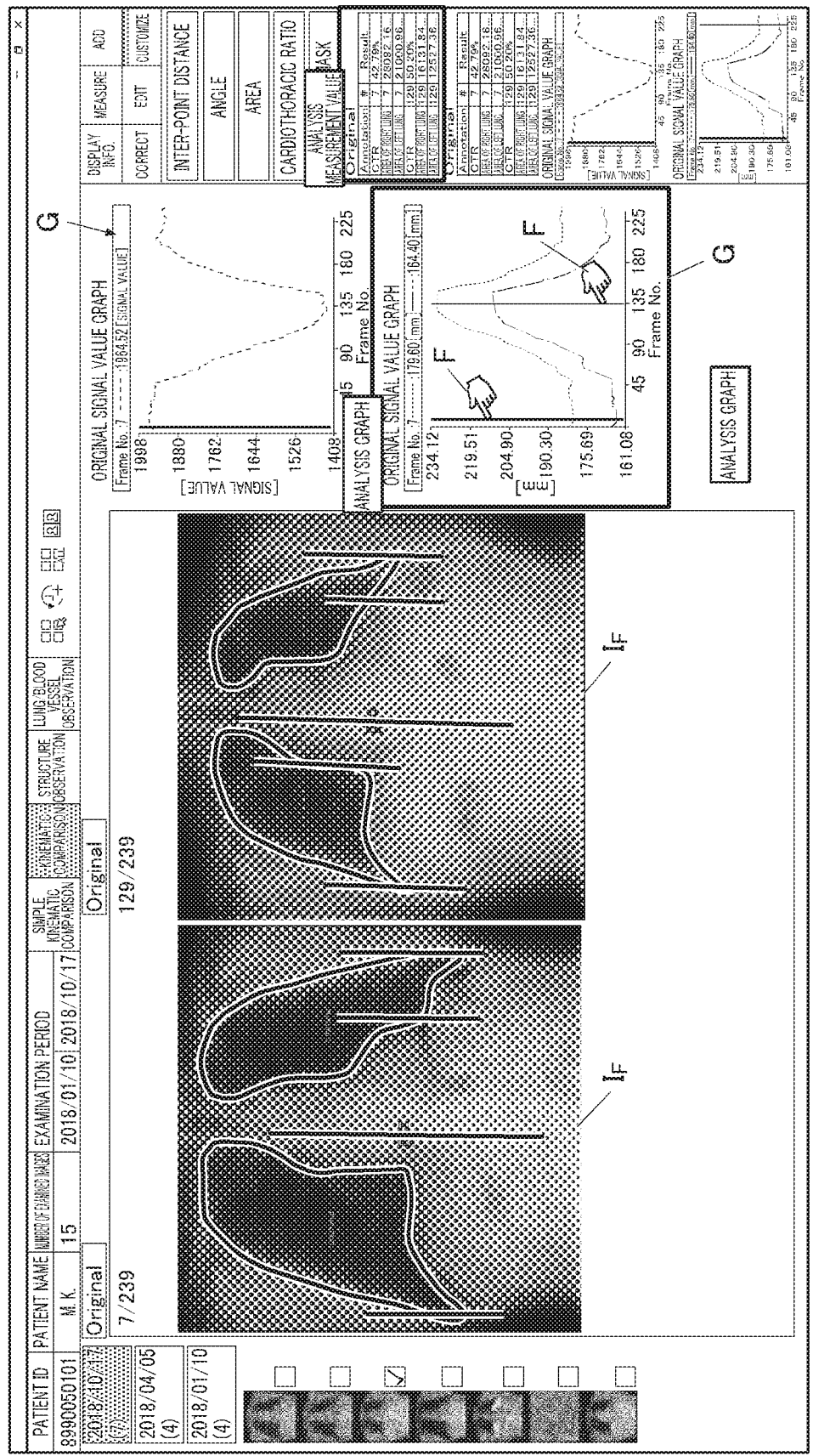
FIG. 12 is an example of a screen displayed on the display device in FIG. 4.

Specifically, as shown in FIG. 12, for example, a frame request signal requesting for a corresponding specific frame image IF is transmitted to the image analysis device 4, on the basis of a touch or a click performed by a finger F or the like on a desired point on a line in the analysis graph G displayed on the display 64.

When the frame request signal is transmitted, data of the specific frame image is transmitted from the analysis device 4 in response to the request, and thus, the controller 61 displays the specific frame image IF according to the request on the display 64.

Additionally, it is also possible to display a plurality of specific frame images F next to each other by specifying a plurality of parts.

Heretofore, a specific configuration of the client 6 according to the present embodiment has been described, but at least a part of various functions of the client 6 described above may be implemented by the console 3, another device including a display, or the like.

As described above, with the image display system 100 according to the present embodiment, data that is most suitable for the purpose of checking, among data of a static image, data of a dynamic image, and analysis result data, is visualized and immediately displayed, and thus, an examining person may perform consultation without having to perform an operation of selecting an analysis result that he/she wants to check, searching for a specific frame image IF in a dynamic image that he/she wants to check, or reproducing a dynamic image and measuring a time taken by predetermined motion, for example. As a result, time taken by consultation using a dynamic image may be reduced compared to a conventional case.

Others

The present invention has been described above with reference to an embodiment, but the present invention is not limited by the embodiment as described above, and may, of course, be changed as appropriate within the scope of the present invention.

Example 1

For example, in the embodiment described above, a dynamic image is reproduced from a first frame and is stopped when a desired frame image is displayed, or a frame image that is displayed is switched, by a touch or a click on a point indicating a desired analysis measurement value on a line in an analysis graph G, to a frame image IF corresponding to the point (see FIG. 12), but in such a case, burden and time are required until a desired specific frame image IF is displayed.

Furthermore, a selected frame image is possibly shifted by several frames from the desired specific frame image IF.

Figure 13A:
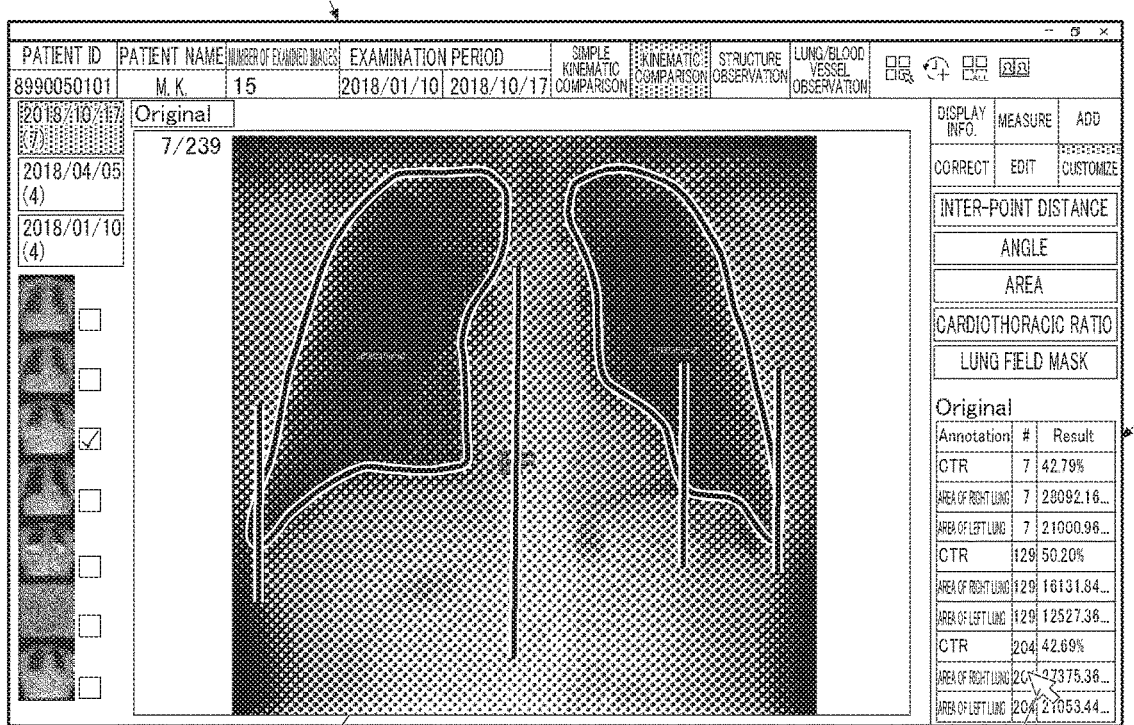
FIG. 13A is an example of a screen displayed on the display device in FIG. 4.
Figure 13B:
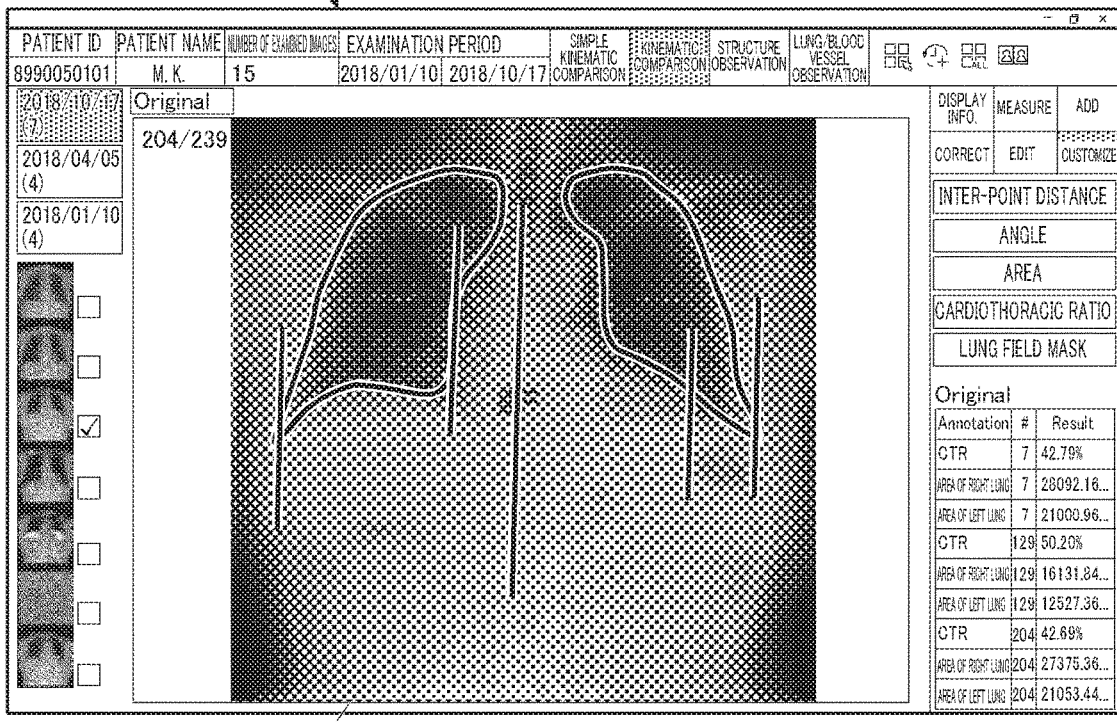
FIG. 13B is an example of a screen displayed on the display device in FIG. 4.

Accordingly, for example, switching to a corresponding specific frame image IF may be performed, as shown in FIG. 13B, on the basis of selection by an operator of an analysis measurement value displayed in the numerical value display section Se or a frame number corresponding to (i.e., displayed near) the analysis measurement value, as shown in FIG. 13A (FIG. 13A shows a case where a cursor C is moved and clicked).

This allows a desired specific frame image IF to be immediately displayed, and time taken to search for a specific frame image IF may be easily reduced, and the consultation time may thus be reduced, compared to a case of reproducing the dynamic image or using the analysis graph G.

Furthermore, because a specific frame image IF is directly selected on the basis of the analysis measurement value, selection/display of a wrong frame image may be easily prevented.

Example 2

For example, in the embodiment described above, a dynamic image is reproduced from a first frame and is stopped when a desired frame image is displayed, or a frame image that is displayed is switched, by a touch or a click on a point indicating a desired analysis measurement value on a line in an analysis graph G, to a frame image corresponding to the point (see FIG. 12), but in such a case, switching to a specific frame image IF where the analysis measurement value takes a local maximum value or a local minimum value in the analysis graph G is burdensome.

Furthermore, a selected frame image is possibly shifted by several frames from the desired specific frame image IF.

Figure 14A:
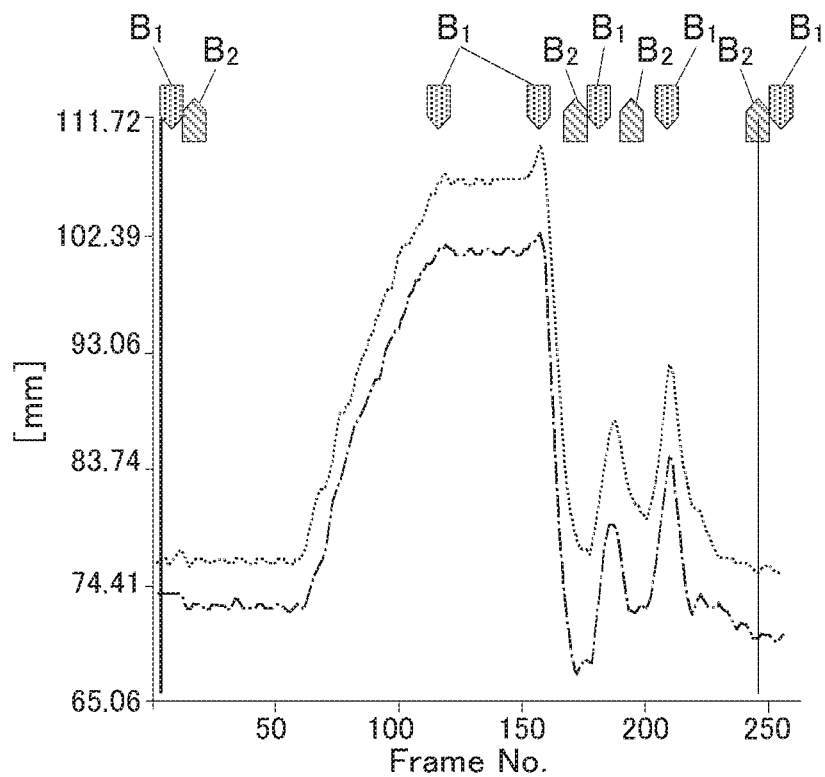
FIG. 14A is an example of an analysis graph displayed on the display device in FIG. 4.

Accordingly, for example, as shown in FIG. 14A, buttons B1, B2 may be provided at parts corresponding to a local maximum and a local minimum in the analysis graph G, and when the button B1 is touched or clicked, switching to a specific frame image IF, corresponding to the button B1, where the analysis measurement value takes the local maximum value in the analysis graph G may be performed, and when the button B2 is touched or clicked, switching to a specific frame image IF, corresponding to the button B2, where the analysis measurement value takes the local minimum value in the analysis graph G may be sequentially performed.

Figure 14B:
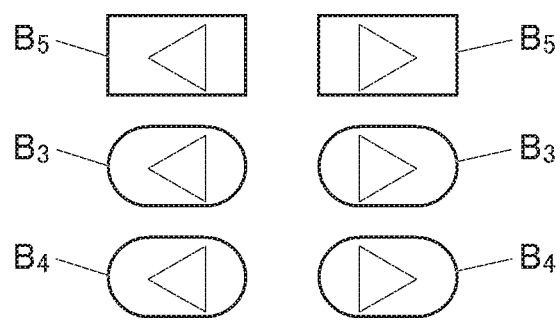
FIG. 14B is an example of buttons provided on the display device in FIG. 4.

Furthermore, pairs of buttons B3, B4 as shown in FIG. 14B, for example, may be provided in the periphery of the check screen S or the display 64 of the client 6, and display may be switched from a currently displayed frame image to a next (previous) specific frame image IF where the analysis measurement value takes the local maximum value in the analysis graph G every time the button B3 on the tight (the left) is touched or clicked, and display may be switched from the currently displayed frame image to a next (previous) specific frame image IF where the analysis measurement value takes the local minimum value in the analysis graph G every time the button B4 on the right (the left) is touched or clicked.

Additionally, as shown in FIG. 14B, a pair of buttons B5 for displaying adjacent frame images regardless of the analysis measurement value may also be provided.

This allows a specific frame image IF where the analysis measurement value takes the local maximum value or the local minimum value in the analysis graph G to be immediately displayed, and time taken to search for a specific frame image IF may be easily reduced, and the consultation time may thus be reduced, compared to a case of reproducing the dynamic image or using the analysis graph G.

Furthermore, because a specific frame image IF is directly selected on the basis of the analysis measurement value, selection/display of a wrong frame image may be easily prevented.

Additionally, a button may be used to switch to a specific frame image IF where the analysis measurement value takes a maximum value, a minimum value, or an average value.

Example 3

For example, if, as in the embodiment described above, a dynamic image is reproduced from a first frame and is stopped when a desired frame image is displayed, or a frame image that is displayed is switched, by a touch or a click on a point indicating a desired analysis measurement value on a line in an analysis graph G, to a frame image corresponding to the point, burden and time are taken until a desired specific frame image IF is displayed, and thus, this is not suitable for use in a case Where time is restricted, such as in a conference.

Figure 15A:
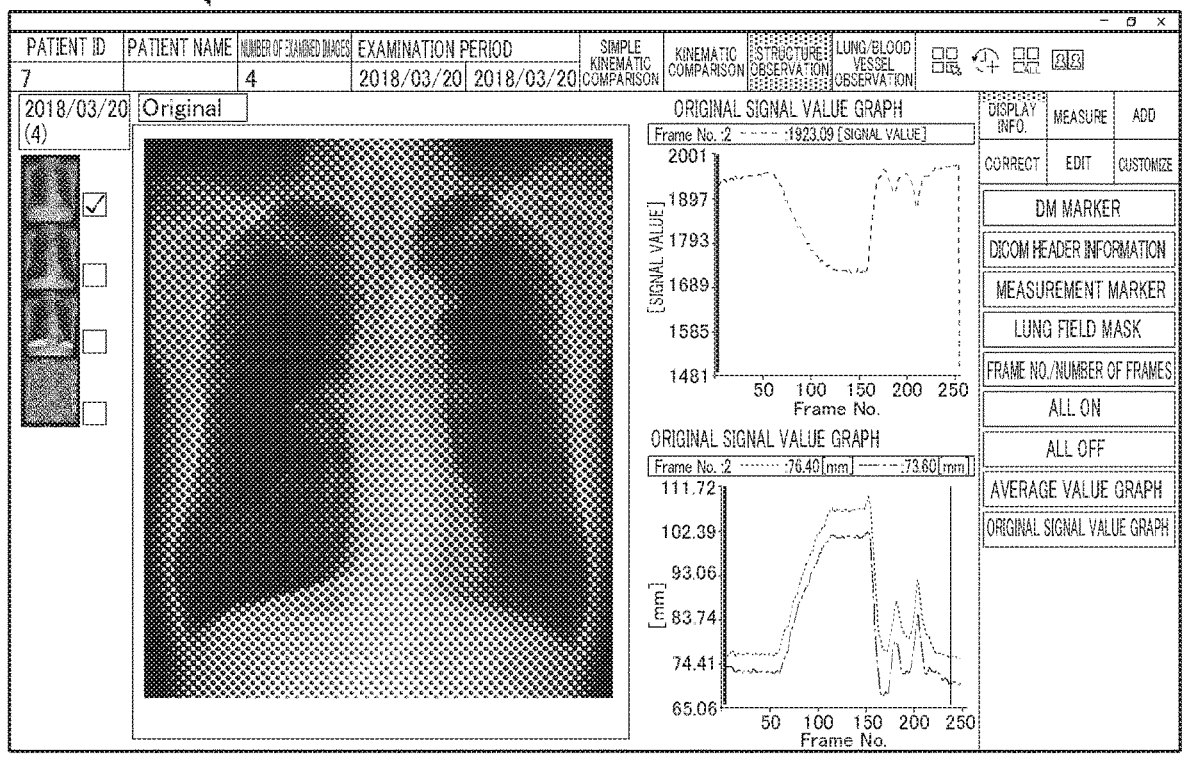
FIG. 15A is an example of a screen displayed on the display device in FIG. 4.
Figure 15B:
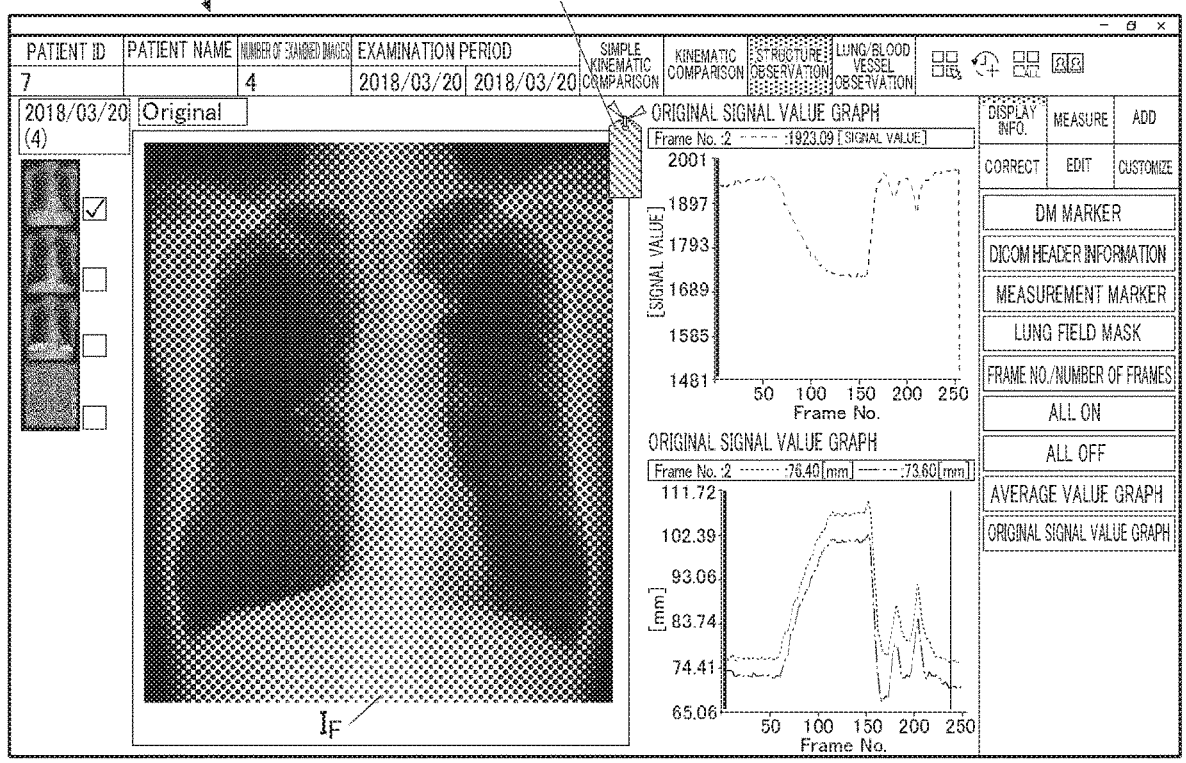
FIG. 15B is an example of a screen displayed on the display device in FIG. 4.

Accordingly, for example, as shown in FIG. 15A, a mark M (bookmark) as shown in FIG. 15B may be attached to a characteristic frame image by performing a predetermined operation (of touching or clicking on the frame image, for example) when the characteristic frame image is displayed, and the frame image to which the mark M is attached may be taken as the specific frame image IF.

Additionally, in the case where the function of attaching the mark M to a frame image is provided, display of only the specific frame image IF to which the mark M is attached may be enabled.

Figure 16:
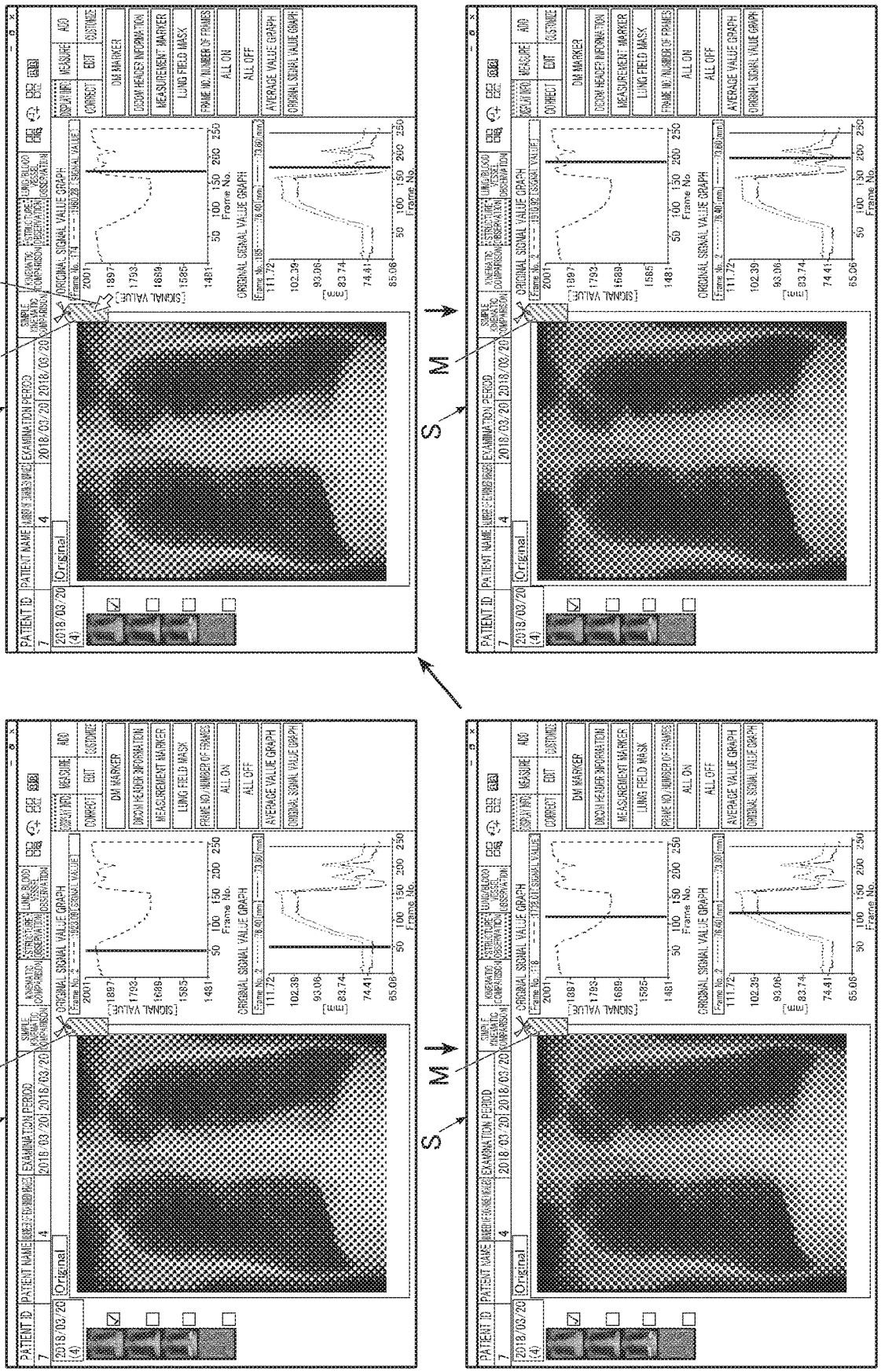
FIG. 16 is an example of a screen displayed on the display device in FIG.

In the case where the mark M is attached to a plurality of specific frame images IF, display may be performed, by a predetermined operation, by jumping to a specific frame image IF to which the mark M is attached, as shown in FIG. 16.

Figure 17:
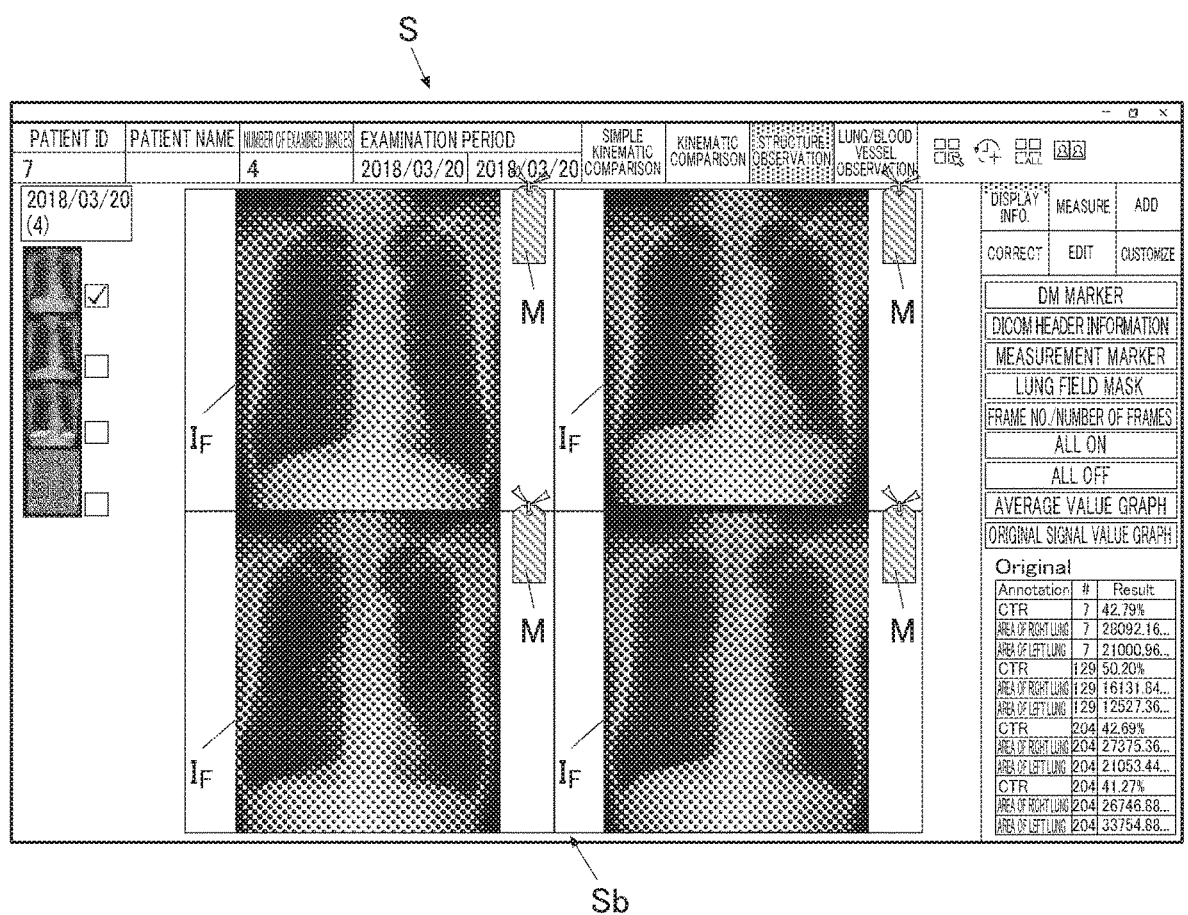
FIG. 17 is an example of a screen displayed on the display device in FIG.

Furthermore, in the case where the mark M is attached to a plurality of specific frame images IF, a list of only the specific frame images IF to which the mark M is attached may be displayed in the image display section Sb, as shown in FIG. 17.

Moreover, in the case where the function of attaching the mark M to a frame image is provided, input of a comment regarding the specific frame image IF (such as a description of the specific frame image IF or an interpretation of the specific frame image IF) may be enabled at the time of attaching the mark M.

Figure 18A:
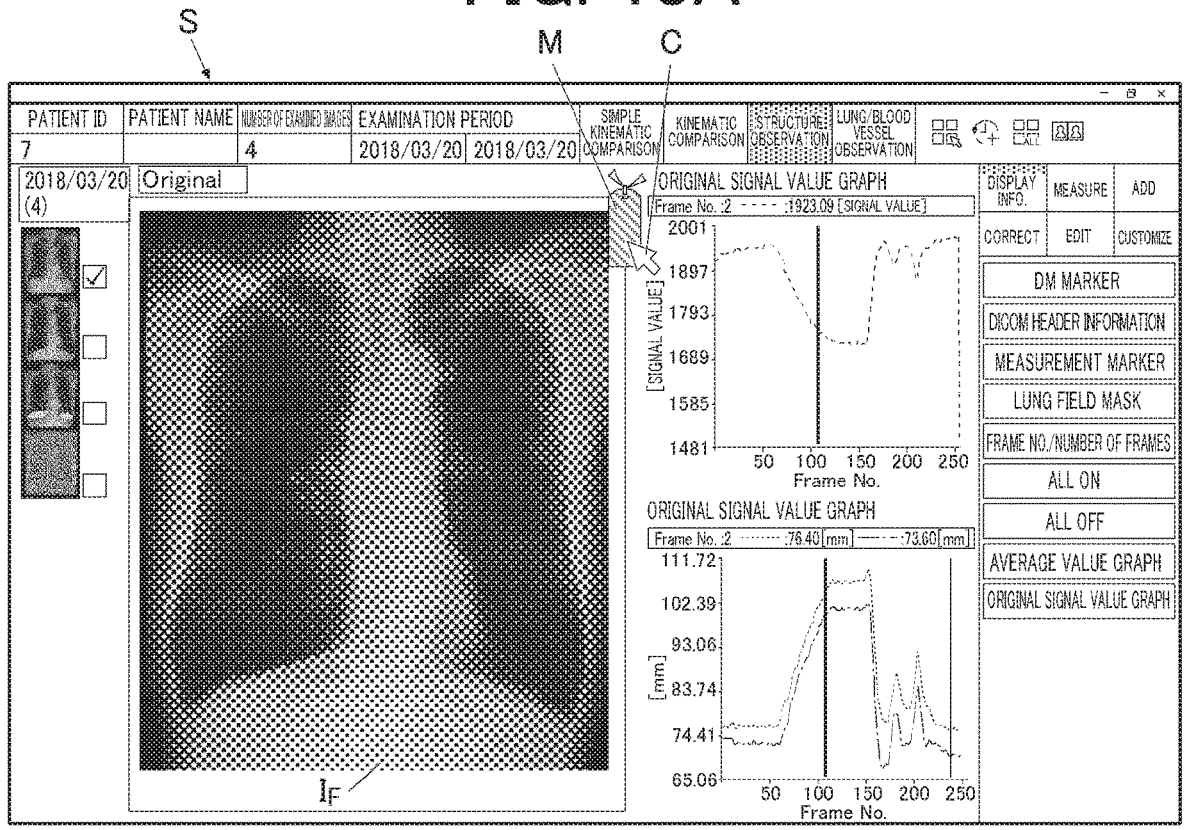
FIG. 18A is an example of a screen displayed on the display device in FIG. 4.
Figure 18B:
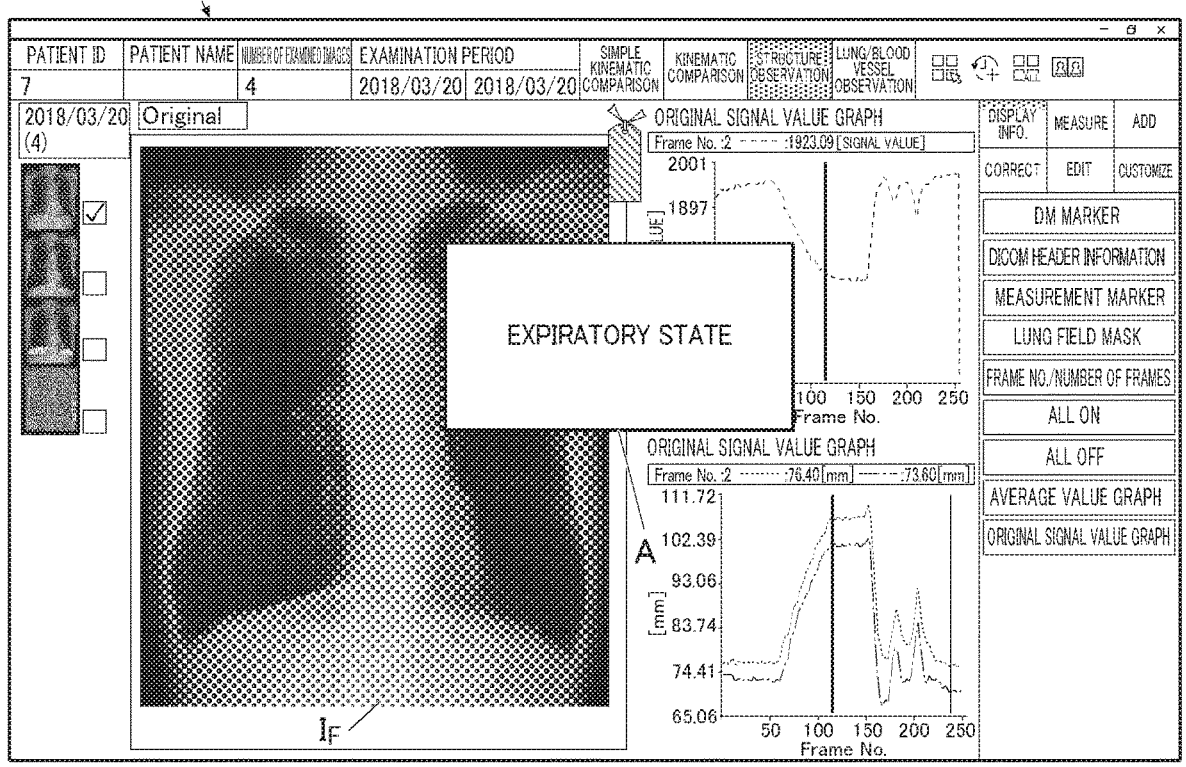
FIG. 18B is an example of a screen displayed on the display device in FIG. 4.

Then, when the specific frame image IF to which the mark M is attached is to be viewed later, a predetermined operation (of touching or clicking on the mark M, for example) may be performed when the specific frame image IF to which the mark M is attached is displayed, as shown in FIG. 18A, for example, and an input comment (a case is shown here where display is performed in the form of the annotation A) may be displayed on the check screen S, together with the specific frame image IF, as shown in FIG. 18B.

The comment may be displayed in the periphery of the specific frame image IF, or may be displayed at least partially superimposed on the specific frame image IF.

Additionally, a display section for text, not shown, may be provided on the check screen S to allow display of the comment in the display section.

A frame image that is not particularly necessary to be displayed is thereby skipped, and a time required for switching of the specific frame image IF may be reduced, and the consultation time may thus be reduced.

Moreover, by displaying the analysis measurement values V in a list, comparison between values may be performed.

Furthermore, a comment may be left as a means for notifying other people or as a reminder.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-218801, filed on 22 of Nov. 2018, is incorporated, herein by reference in its entirety.

What is claimed is:

1. An image display control system comprising a hardware processor configured to:
   acquire data of a dynamic image of a subject including a plurality of frame images,
   analyze the data of the dynamic image, and create analysis result data,
   specify a purpose of checking from among a plurality of different purposes of checking stored in advance,
   display, on a display device, a plurality of operation buttons respectively corresponding to the plurality of different purposes of checking, wherein an operation button corresponding to the specified purpose of checking among the plurality of operation buttons is displayed in a changed display state as compared to operation buttons among the plurality of operation buttons that correspond to purposes of checking other than the specified purpose of checking, wherein the plurality of operation buttons are operable to switch the specified purpose of checking, and
   select and display on the display device, based on the specified purpose of checking, at least one from the dynamic image based on the data of the dynamic image and a dynamic analysis image based on the analysis result data, and at least one from an analysis value based on the analysis result data and an analysis graph based on the analysis result data,
   wherein the hardware processor is configured to acquire, from a memory, a correspondence relationship between examination target parts and the plurality of different purposes of checking that can be selected for the examination target parts, and to enable or disable selection of each of the plurality of operation buttons based on the acquired correspondence relationship and an examination target part corresponding to the subject in the dynamic image.

2. The image display control system according to claim 1, wherein:
   the hardware processor selects the analysis graph, and
   the analysis graph is a graph showing change over time among the plurality of frame images.

3. The image display control system according to claim 1, wherein the analysis graph is a graph created based on the analysis value.

4. The image display control system according to claim 1, further comprising the memory,
   wherein the memory stores at least one type of the analysis result data in association with each of the plurality of different purposes of checking,
   wherein the hardware processor is further configured to:
      create a plurality of pieces of analysis result data of different types, and
      select the data that is associated with the specified purpose of checking, among the data of the dynamic image, and the plurality of pieces of analysis result data.

5. The image display control system according to claim 4, wherein the memory stores, in association with each of the plurality of different purposes of checking, at least one of a number of displays used for display, a button to be displayed, a layout of a screen, a display timing of data, a display order of data, a display time of data, a display size, a color scheme at a time of display, assignment of a function to an operation unit, and a radiographing period of an image.

6. The image display control system according to claim 1, wherein the plurality of different purposes of checking include at least two of kinematic comparison of comparing a still subject and a moving subject, kinematic comparison of comparing a subject in a certain state and the subject in another state, structure observation of observing motion of a specific structure in a subject, blood vessel observation of observing a state of a blood vessel in a subject, follow-up observation of observing a change in a state of a subject from a past state, and emergency of specifying an abnormal part of an emergency patient.

7. The image display control system according to claim 1, wherein the hardware processor causes the purpose of checking to be specified automatically based on the analysis result data that is created or examination information, or manually based on an operation performed by an operator before or after acquisition of the dynamic image.

8. The image display control system according to claim 1, wherein the hardware processor selects a specific frame image that is specified based on analysis result from a plurality of frame images forming the dynamic image or the dynamic analysis image.

9. The image display control system according to claim 8, wherein the specific frame image is a frame image, among the plurality of frame images, that is a frame image where the analysis value is greatest, a frame image where the analysis value is smallest, a frame image, the analysis value of which coincides with an average value, a frame image, the analysis value of which is within a predetermined range, a frame image, the analysis value of which coincides with a predetermined value, or a frame image selected by an operator.

10. The image display control system according to claim 8, wherein the specific frame image is a frame image, among the plurality of frame images, that is a frame image, the analysis value of which is closest to an analysis value of a static image, or a frame image, the analysis value of which is farthest from the analysis value of a static image.

11. The image display control system according to claim 1, wherein the analysis value includes at least one of a position of a specific point of a specific structure of the subject, a distance between the specific point and another point, an area of the specific structure, a volume of the specific structure, a signal value of a predetermined pixel of the subject, a maximum signal value in a predetermined range in the frame image, a minimum signal value in the predetermined range, an average value of all signal values in the predetermined range, a cardiothoracic ratio, and an arrangement angle of the specific structure in the frame image.

12. The image display control system according to claim 1, wherein the hardware processor selects, based on the specified purpose of checking and examination information, at least one from a dynamic image based on the data of the dynamic image, and a dynamic analysis image based on the analysis result data.

13. The image display control system according to claim 7, wherein the examination information includes at least one of a type of radiographing, a radiographing target part, a name of a clinical department requesting for examination, age of an examined person, sex of the examined person, and a name of an operator.

14. The image display control system according to claim 12, wherein the examination information includes at least one of a type of radiographing, a radiographing target part, a name of a clinical department requesting for examination, age of an examined person, sex of the examined person, and a name of an operator.

15. An image display system comprising:
an image display control system according to claim 1; and
the display device that displays at least one from the dynamic image based on data of the dynamic image and a dynamic analysis image based on the analysis result data, and at least one from an analysis value based on the analysis result data and an analysis graph based on the analysis result data.

16. The image display system according to claim 15, wherein the hardware processor:
changes the purpose of checking that is set, based on an operation performed by an operator, and
switches, according to change of the purpose of checking, a layout of a check screen to a layout that is in accordance with the purpose of checking after the change.

17. An image analysis device comprising a hardware processor configured to:
acquire data of a dynamic image of a subject including a plurality of frame images,
analyze the data of the dynamic image and create analysis result data,
specify a purpose of checking from among a plurality of different purposes of checking stored in advance,
display, on a display device, a plurality of operation buttons respectively corresponding to the plurality of different purposes of checking, wherein an operation button corresponding to the specified purpose of checking among the plurality of operation buttons is displayed in a changed display state as compared to operation buttons among the plurality of operation buttons that correspond to purposes of checking other than the specified purpose of checking, wherein the plurality of operation buttons are operable to switch the specified purpose of checking, and
select and display on the display device, based on the purpose of checking, at least one from the dynamic image based on the data of the dynamic image and a dynamic analysis image based on the analysis result data, and at least one from an analysis value based on the analysis result data and an analysis graph based on the analysis result data,
wherein the hardware processor is configured to acquire, from a memory, a correspondence relationship between examination target parts and the plurality of different purposes of checking that can be selected for the examination target parts, and to enable or disable selection of each of the plurality of operation buttons based on the acquired correspondence relationship and an examination target part corresponding to the subject in the dynamic image.

18. A non-transitory computer-readable storage medium having stored thereon a program which, when executed by a computer, causes the computer to perform operations of:
acquiring data of a dynamic image of a subject including a plurality of frame images,
analyzing the data of the dynamic image, and creating analysis result data,
specifying a purpose of checking from among a plurality of different purposes of checking stored in advance,
displaying, on a display device, a plurality of operation buttons respectively corresponding to the plurality of different purposes of checking, wherein an operation button corresponding to the specified purpose of checking among the plurality of operation buttons is displayed in a changed display state as compared to operation buttons among the plurality of operation buttons that correspond to purposes of checking other than the specified purpose of checking, wherein the plurality of operation buttons are operable to switch the specified purpose of checking,
selecting and displaying on the display device, based on the purpose of checking, at least one from the dynamic image based on the data of the dynamic image and a dynamic analysis image based on the analysis result data, and at least one from an analysis value based on the analysis result data and an analysis graph based on the analysis result data, and
acquiring, from a memory, a correspondence relationship between examination target parts and the plurality of different purposes of checking that can be selected for the examination target parts, and enabling or disabling selection of each of the plurality of operation buttons based on the acquired correspondence relationship and an examination target part corresponding to the subject in the dynamic image.

19. An image display control method comprising:
acquiring data of a dynamic image of a subject including a plurality of frame images,
analyzing the data of the dynamic image, and creating analysis result data,
specifying a purpose of checking from among a plurality of different purposes of checking stored in advance,
displaying, on a display device, a plurality of operation buttons respectively corresponding to the plurality of different purposes of checking, wherein an operation button corresponding to the specified purpose of checking among the plurality of operation buttons is displayed in a changed display state as compared to operation buttons among the plurality of operation buttons that correspond to purposes of checking other than the specified purpose of checking, wherein the plurality of operation buttons are operable to switch the specified purpose of checking, selecting and displaying on the display device, based on the purpose of checking, at least one from the dynamic image based on the data of the dynamic image and a dynamic analysis image based on the analysis result data, and at least one from an analysis value based on the analysis result data and an analysis graph based on the analysis result data, and acquiring, from a memory, a correspondence relationship between examination target parts and the plurality of different purposes of checking that can be selected for the examination target parts, and enabling or disabling selection of each of the plurality of operation buttons based on the acquired correspondence relationship and an examination target part corresponding to the subject in the dynamic image.

20. The image display control system according to claim 1, wherein the hardware processor is further configured to select, from among a plurality of layouts stored in advance in association with the plurality of different purposes of checking, respectively, a layout associated with the specified purpose of checking.

\* \* \* \* \*